(12) United States Patent
Vianello et al.

(10) Patent No.: US 10,233,165 B2
(45) Date of Patent: Mar. 19, 2019

(54) CYCLOPROPYLAMINE COMPOUNDS AS HISTONE DEMETHYLASE INHIBITORS

(71) Applicant: IEO—Instituto Europeo di Oncologia S.r.l., Milan (IT)

(72) Inventors: Paola Vianello, Milan (IT); Mario Varasi, Milan (IT); Ciro Mercurio, Legnano (IT); Anna Cappa, Visso (IT); Giuseppe Meroni, Milan (IT); Manuela Villa, Lurago d'Erba (IT); Antonello Mai, Rome (IT); Sergio Valente, Cassino (IT)

(73) Assignee: Istituto Europeo di Oncologia S.r.l., Milan (IT)

( * ) Notice: Subject to any disclaimer, the term of this patent is extended or adjusted under 35 U.S.C. 154(b) by 0 days.

(21) Appl. No.: 15/314,851

(22) PCT Filed: May 29, 2015

(86) PCT No.: PCT/EP2015/062037
§ 371 (c)(1),
(2) Date: Nov. 29, 2016

(87) PCT Pub. No.: WO2015/181380
PCT Pub. Date: Dec. 3, 2015

(65) Prior Publication Data
US 2017/0190680 A1 Jul. 6, 2017

(30) Foreign Application Priority Data

May 30, 2014 (EP) .................................. 14170656
Nov. 14, 2014 (EP) .................................. 14193312

(51) Int. Cl.
| | | |
|---|---|---|
| A61K 31/421 | (2006.01) | |
| A61K 31/445 | (2006.01) | |
| A61K 31/495 | (2006.01) | |
| A61K 31/5375 | (2006.01) | |
| A61K 45/06 | (2006.01) | |
| C07D 211/14 | (2006.01) | |
| C07D 211/34 | (2006.01) | |
| C07D 241/04 | (2006.01) | |
| C07D 263/22 | (2006.01) | |
| C07D 265/30 | (2006.01) | |
| C07D 295/155 | (2006.01) | |

(52) U.S. Cl.
CPC ........ *C07D 295/155* (2013.01); *A61K 31/421* (2013.01); *A61K 31/445* (2013.01); *A61K 31/495* (2013.01); *A61K 31/5375* (2013.01); *A61K 45/06* (2013.01); *C07D 211/14* (2013.01); *C07D 211/34* (2013.01); *C07D 241/04* (2013.01); *C07D 263/22* (2013.01); *C07D 265/30* (2013.01)

(58) Field of Classification Search
CPC combination set(s) only.
See application file for complete search history.

(56) References Cited

U.S. PATENT DOCUMENTS

2010/0324147 A1   12/2010   McCafferty et al.
2014/0228405 A1*   8/2014   Tomita et al. ........ C07C 233/80

FOREIGN PATENT DOCUMENTS

| GB | 2404658 A | 2/2005 |
|---|---|---|
| WO | WO 2003/045913 A1 | 6/2003 |
| WO | WO 2006/092510 A1 | 9/2006 |
| WO | WO 2009/055077 A1 | 4/2009 |
| WO | 2011/131576 A1 | 10/2011 |
| WO | WO 2011/131576 A1 | 10/2011 |
| WO | WO 2012/045883 A1 | 4/2012 |
| WO | WO-2013022047 A1 * | 2/2013 ........... A61K 31/167 |

OTHER PUBLICATIONS

Benelkebir, H. et al. "Enantioselective synthesis of tranylcypromine analogues as lysine demethylase (LSD1) inhibitors", *Bioorganic & Medicinal Chemistry*, 2011, vol. 19, pp. 3709-3716.

Binda C. et al. "Insights into the mode of inhibition of human mitochondrial monoamine oxidase B from high-resolution crystal structures", *Proc. Natl. Acad. Sci. USA*, 2003, pp. 9750-9755.

Binda C. et al. "Biochemical, Structural, and Biological Evaluation of Tranylcypromine Derivatives as Inhibitors of Histone Demethylases LSD1 and LSD2", *J. Am. Chem. Soc.*, 2010, vol. 132, pp. 6827-6833.

Bujok, R. et al. "Novel approach to synthesis of substituted 3-aminoquinolines from nitroarenes and protected ethyl aminocrotonate", *Tetrahedron*, 2010, vol. 66, pp. 698-708.

Christiansen, E. et al. "Free Fatty Acid Receptor 1 (FFA1/GPR40) Agonists: Mesylpropoxy Appendage Lowers Lipophilicity and Improves ADME Properties", *Journal of Medicinal Chemistry*, 2012, vol. 55, pp. 6624-6628.

(Continued)

*Primary Examiner* — Amanda L Aguirre
(74) *Attorney, Agent, or Firm* — Cooley LLP; Heidi A. Erlacher; Thomas J. Paxton

(57) ABSTRACT

The present disclosure relates to cyclopropyl compounds of general formula (I), wherein $R^1$, and $R^2$ are as defined in the specification. The present application also relates to pharmaceutical compositions containing such compounds and to their use in therapy.

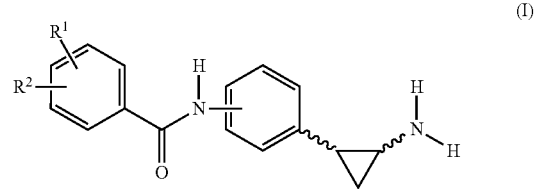

(I)

32 Claims, 2 Drawing Sheets
Specification includes a Sequence Listing.

(56) References Cited

OTHER PUBLICATIONS

Denney, D. et al. "Formation of Cyclopropanes From Phosphoranes and Epoxides" *J. Am. Chem. Soc.*, 1959, vol. 81, pp. 6330-6331.
Forneris, F. et al. "LSD1: oxidative chemistry for multifaceted functions in chromatin regulation", *Trends Biochem. Sci.*, 2008, vol. 33, pp. 181-189.
Forneris, F. et al. "Structural Basis of LSD1-CoREST Selectivity in Histone H3 Recognition", *J. Biol. Chem.*, 2007, vol. 282, pp. 20070-20074.
Gooden, D. et al. "Facile synthesis of substituted trans-2-arylcyclopropylamine inhibitors of the human histone demethylase LSD1 and monoamine oxidases A and B", *Bioorganic & Medicinal Chemistry Letters*, 2008, vol. 18, pp. 3047-3051.
Harris, W. et al. "The Histone Demethylase KDM1A Sustains the Oncogenic Potential of MLL-AF9 Leukemia Stem Cells", *Cancer Cell*, 2012, vol. 21, pp. 473-487.
Hino S. et al. "FAD-dependent lysine-specific demethylase-1 regulates cellular energy expenditure", *Nature Communications*, 2012, doi:10.1038/ncomms1755, 12 pages.
Lakshminarayana, N. et al. "Synthesis and evaluation of some novel dibenzo[b,d]furan carboxylic acids as potential anti-diabetic agents", *European Journal of Medicinal Chemistry*, 2010, vol. 45, pp. 3709-3718.
Minucci, S. et al. "PML-RAR induces promyelocytic leukemias with high efficiency following retroviral gene transfer into purified murine hematopoietic progenitors", *Blood*, 2002, vol. 100, pp. 2989-2995.
Saleque, S. et al. "Epigenetic Regulation of Hematopoietic Differentiation by Gfi-1 and Gfi-1b Is Mediated by the Cofactors CoREST and LSD1", *Molecular Cell*, 2007, vol. 27, pp. 562-572.
PCT International Search Report issued for PCT/EP2015/062037 and dated Aug. 12, 2015 (4 pages).
Rotili, D. et al. "Pan-Histone Demethylase Inhibitors Simultaneously Targeting Jumonji C and Lysine-Specific Demethylases Display High Anticancer Activities", *Journal of Medicinal Chemistry*, 2014, vol. 57, pp. 42-55.

\* cited by examiner

CYCLOPROPYLAMINE COMPOUNDS AS HISTONE DEMETHYLASE INHIBITORS

CROSS-REFERENCE TO RELATED APPLICATIONS

This application is a national phase entry of PCT Application No. PCT/EP2015/062037, filed May 29, 2015, which claims priority to, and the benefit of, European Patent Application No. 14193312.7, filed Nov. 14, 2014, and European Patent Application No. 14170656.4, filed May 30, 2014, the contents of each of which are incorporated herein by reference in their entirety.

FIELD OF THE DISCLOSURE

The present invention relates to cyclopropyl compounds, pharmaceutical compositions containing such compounds and to their use in therapy.

BACKGROUND

Alterations in the structural and functional states of chromatin, mainly determined by post-translational modification of histone components, are involved in the pathogenesis of a variety of diseases. The enzymatic processes governing these post-translational modifications on the nucleosomes have become potential targets for the so-called epigenetic therapies (Portela, A. et al. Nat. Biotechnol. 2010, 28, 1057-1068).

The discovery of an increasing number of histone lysine demethylases has highlighted the dynamic nature of the regulation of histone methylation, a key chromatin modification that is involved in eukaryotic genome and gene regulation. Histone lysine demethylases represent attractive targets for epigenetic drugs, since their expression and/or activities are often misregulated in cancer (Varier, R. A. et al. Biochim. Biophys. Acta. 2011, 1815, 75-89). A lysine can be mono-, di-, and tri-methylated and each modification, even on the same amino acid, can exert different biological effects.

Histone lysine demethylases exert their activity through two different type of mechanism (Anand, R. et al. J. Biol. Chem. 2007, 282, 35425-35429; Metzger, E. et al. Nat. Struct. Mol. Biol. 2007, 14, 252-254). While the Jumonji domain-containing histone demethylases, which are iron and 2-oxoglutarate dependent oxygenases, act on mono-, di- and trimethylated lysines, the flavin-dependent (FAD) histone demethylases catalyse the cleavage of mono and dimethylated lysine residues. Currently, two FAD dependent demethylases have been identified: LSD1, also known as KDM1A, and LSD2, also known as KDM1B. (Culhane, J. C. et al. Curr Opin Chem Biol 2007, 11, 561-568, Ciccone, D. N. et al. Nature 2009, 461, 415-418).

KDM1A is a constituent in several chromatin-remodeling complexes and is often associated with the co-repressor protein CoREST. KDM1A specifically removes the methyl groups from both mono- and di-methyl Lys4 of histone H3, which is a well-characterized gene activation mark.

KDM1A represents an interesting target for epigenetic drugs as supported by data related to its over-expression in solid and hematological tumors (Schulte, J. H. et al. Cancer Res. 2009, 69, 2065-2071; Lim, S. et al. Carcinogenesis 2010, 31, 512-520; Hayami, S. et al. Int. J. Cancer 2011, 128, 574-586; Schildhaus, H. U. et al. Hum. Pathol. 2011, 42, 1667-1675; Bennani-Baiti, I. M. et al. Hum. Pathol. 2012, 43, 1300-1307). Its over-expression correlates to tumor recurrence in prostate cancer (Kahl, P. et al. Cancer Res. 2006, 66, 11341-11347), and has a role in various differentiation processes, such as adipogenesis (Musri, M. M. et al. J. Biol. Chem. 2010, 285, 30034-30041), muscle skeletal differentiation (Choi, J. et al. Biochem. Biophys. Res. Commun. 2010, 401, 327-332), and hematopoiesis (Hu, X. et al. Proc. Natl. Acad. Sci. USA 2009, 106, 10141-10146; Li, Y. et al. Oncogene 2012, 31, 5007-18). KDM1A is further involved in the regulation of cellular energy expenditure (Hino S. Et al. Nat Commun. 2012, doi: 10.1038/ncomms1755), in the control of checkpoints of viral gene expression in productive and latent infections (Roizman, B. J. Virol. 2011, 85, 7474-7482) and more specifically in the control of herpes virus infection (Gu, H. J. Virol. 2009, 83, 4376-4385) and HIV transcription (Sakane, N. et al. PLoS Pathog. 2011, 7(8):e1002184). The role of KDM1A in the regulation of neural stem cell proliferation (Sun, G. et al. Mol. Cell Biol. 2010, 30, 1997-2005) as well as in the control of neuritis morphogenesis (Zibetti, C. et al. J. Neurosci. 2010, 30, 2521-2532) suggests its possible involvement in neurodegenerative diseases.

Furthermore, there are evidences of the relevance of KDM1A in the control of other important cellular processes, such as DNA methylation (Wang, J. et al. Nat. Genet. 2009, 41(1):125-129), cell proliferation (Scoumanne, A. et al. J. Biol. Chem. 2007, 282, 15471-15475; Cho, H. S. et al. Cancer Res. 2011, 71, 655-660), epithelial mesenchimal transition (Lin, T. et al. Oncogene. 2010, 29, 4896-4904) and chromosome segregation (Lv, S. et al. Eur. J. Cell Biol. 2010, 89, 557-563). Moreover, it was found that KDM1A inhibitors were able to reactivate silenced tumor suppressor genes (Huang, Y. et al. Proc. Natl. Acad. Sci. USA. 2007, 104, 8023-8028; Huang, Y. et al. Clin. Cancer Res. 2009, 15, 7217-7228), to target selectively cancer cells with pluripotent stem cell properties (Wang, J. et al. Cancer Res. 2011, 71, 7238-7249), as well as to reactivate the all-trans-retinoic acid differentiation pathway in acute myeloid leukemia (Schenk, T. et al. Nat Med. 2012, 18, 605-611).

The more recently discovered demethylase KDM1B (LSD2) displays—similarly to KDM1A—specificity for mono- and di-methylated Lys4 of histone H3. KDM1B, differently from KDM1A, does not bind CoREST and it has not been found up to now in any of KDM1A-containing protein complex (Karytinos, A. et al. J. Biol. Chem. 2009, 284, 17775-17782). On the contrary, KDM1B forms active complexes with euchromatic histone methyltransferases G9a and NSD3 as well as with cellular factors involved in transcription elongation. KDM1B has been reported to have a role as regulator of transcription elongation rather than that of a transcriptional repressor as proposed for KDM1A (Fang, R. et al. Mol. Cell 2010, 39, 222-233).

KDM1A and KDM1B are both flavo amino oxidase dependent proteins sharing a FAD coenzyme-binding motif, a SWIRM domain and an amine oxidase domain, all of which are integral to the enzymatic activity of KDM1 family members. Moreover, both KDM1A and KDM1B show a structural similarity with the monoamine oxidases MAO-A and MAO-B.

Indeed, tranylcypromine, a MAO inhibitor used as antidepressant agent, was found to be also able to inhibit LSD1. The compound acts as an irreversible inhibitor forming a covalent adduct with the FAD cofactor. (Lee, M. G. et al. Chem. Biol. 2006, 13, 563; Schmidt, D. M. Z. et al. Biochemistry 2007, 46, 4408).

The synthesis of tranylcypromine analogs and their LSD1 inhibitory activity has been described in Bioorg. Med. Chem. Lett. 2008, 18, 3047-3051, in Bioorg. Med. Chem.

2011, 19, 3709-3716, and in J. Am. Chem. Soc. 2011, 132, 6827-6833. Further arylcyclopropylamine and heteroarylcyclopropylamine derivatives as LSD1, MAO-A and/or MAO-B enzyme inhibitors are disclosed in US2010/324147, in WO2012/045883 and in WO2013/022047.

WO2011/131576 discloses tranylcyclopropylamine compounds of the general formula

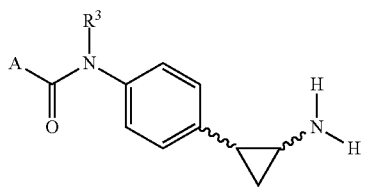

wherein A is R or CH(R1)-NH—CO—R2; R and R2 are selected from: alkyl, alkenyl, alkynyl, cycloalkyl, aryl, heteroaryl, heterocycloalkyl, cycloalkylalkyloxy, arylalkyloxy, heteroarylalkyloxy, heterocycloalkylalkyloxy, cycloalkylalkyl, arylalkyl, heteroarylalkyl, heterocycloalkylalkyl, cycloalkylalkylamino, arylalkylamino, heteroarylalkylamino, heterocycloalkylalkylamino; R1 is selected from: alkyl, alkenyl, alkynyl, cycloalkyl, aryl, heteroaryl, heterocycloalkyl, cycloalkylalkyl, arylalkyl, heteroarylalkyl, heterocycloalkylalkyl; and R3 is H, lower alkyl.

However, there is still the need for compounds endowed with inhibitory activity on KDM1A and/or KDM1B enzyme activity with a low inhibitory activity on MAOA and/or MAOB enzymes.

MAOs are well known targets for the treatment of diseases of the central nervous system, such as depression or Parkinson's disease. However, inhibition of the MAOs are associated with side effects, among them tyramine-induced hypertensive crisis or the serotonin syndrome, which occurs in situation of concomitant use of MAO inhibitors 882; Iqbal, M. M. Ann Clin Psychiatry, 2012, 24, 310-318).

SUMMARY OF THE DISCLOSURE

The present disclosure relates to substituted cyclopropylamine compounds which may have highly potent activities of the KDM1A enzyme and/or of the KDM1B enzyme and low inhibitory activity of monoamine oxidases (MAOs).

In one aspect, the present disclosure relates to compounds which inhibit KDM1.

In one aspect, the present disclosure relates to compounds that inhibit KDM1A and/or KDM1B enzymes to a greater degree than MAOs.

In one aspect, the present disclosure relates to compounds for the prevention or therapy of diseases and conditions associated with the activity of the histone demethylases.

In one aspect, the present disclosure relates to compounds of general formula (I)

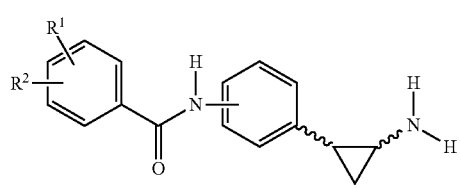

or a pharmaceutically acceptable salt, solvate, or prodrug thereof.

In one aspect $R^1$ is heterocyclyl or heterocyclyl substituted by oxo, wherein the heterocyclyl is unsubstituted or substituted by one or more $C_1$-$C_6$ alkyl groups.

In another aspect, $R^1$ is pyrrolidinyl, piperidinyl, piperazinyl, tetrahydrofuranyl, tetrahydropyranyl, morpholinyl, thiomorpholinyl, tetrahydroquinolinyl, tetrahydroisoquinolinyl, tetrahydroquinoxalinyl, benzodioxolyl, 2,3-dihydrobenzodioxinyl, benzoxazolyl, azepinyl, diazapinyl or 2-oxooxazolidinyl, wherein each is unsubstituted or substituted by one or more $C_1$-$C_6$ alkyl groups.

In another aspect, $R^1$ is 4-methylpiperazin-1-yl, 1-methylpiperidin-4-yl, piperidin-1-yl, or 2-oxooxazolidin-3-yl.

In one aspect $R^2$ is hydrogen, halogen, $C_1$-$C_6$ alkyl, $C_1$-$C_6$ alkoxy, $C_1$-$C_6$ haloalkyl, or $C_1$-$C_6$ haloalkoxy, or benzyloxycarbonylamino.

In one aspect $R^2$ is selected from the group consisting of hydrogen or benzyloxycarbonylamino.

In one aspect, the compound of the disclosure is selected from:
N-[4-[trans-2-aminocyclopropyl]phenyl]-4-(4-methylpiperazin-1-yl)benzamide;
N-[4-[trans-2-aminocyclopropyl]phenyl]-4-(1-methyl-4-piperidyl)benzamide;
N-[4-[trans-2-aminocyclopropyl]phenyl]-3-(2-oxooxazolidin-3-yl)benzamide;
N-[4-[trans-2-aminocyclopropyl]phenyl]-4-morpholino-benzamide;
N-[4-[trans-2-aminocyclopropyl]phenyl]-4-(2-oxooxazolidin-3-yl)benzamide;
benzyl N-[5-[[4-[(trans-2-aminocyclopropyl)phenyl]carbamoyl]-2-(4-methylpiperazin-1-yl)phenyl]carbamate;
benzyl N-[4-[[4-[trans-2-aminocyclopropyl]phenyl]carbamoyl]-2-(4-methylpiperazin-1-yl)phenyl]carbamate;
benzyl N-[5-[[4-[trans-2-aminocyclopropyl]phenyl]carbamoyl]-2-(1-piperidyl)phenyl]carbamate;
benzyl N-[5-[[4-[trans-2-aminocyclopropyl]phenyl]carbamoyl]-2-morpholino-phenyl]carbamate;
N-[4-[(1S,2R)-2-aminocyclopropyl]phenyl]-4-(4-methylpiperazin-1-yl)benzamide;
N-[4-[(1S,2R)-2-aminocyclopropyl]phenyl]-3-(2-oxooxazolidin-3-yl)benzamide;
N-[4-[(1R,2S)-2-aminocyclopropyl]phenyl]-4-(4-methylpiperazin-1-yl)benzamide;
N-[4-[(1R,2S)-2-aminocyclopropyl]phenyl]-3-(2-oxooxazolidin-3-yl)benzamide; or
a pharmaceutically acceptable salt, solvate, or prodrug thereof.

In one aspect, the disclosure relates to a pharmaceutical composition comprising a compound of the disclosure, or a pharmaceutically acceptable salt, solvate, or prodrug thereof and a pharmaceutically acceptable carrier and/or diluent.

In one aspect, the disclosure relates to a method of preventing or treating a disease or disorder comprising administering to a subject in need thereof an effective amount of a compound of the disclosure, or a pharmaceutically acceptable salt, solvate, or prodrug thereof, or a pharmaceutical composition of the disclosure.

In one aspect, the application relates to the use of a compound of the disclosure, or a pharmaceutically acceptable salt, solvate, or prodrug thereof, or a pharmaceutical composition of the disclosure for preventing or treating a disease or disorder in a subject in need thereof.

In one aspect, the disclosure relates to the use of a compound of the disclosure, or a pharmaceutically acceptable salt, solvate, or prodrug thereof, or a pharmaceutical composition of the disclosure in the manufacture of a medicament for preventing or treating a disease or disorder in a subject in need thereof.

In one aspect, the compounds of the disclosure are for use in the treatment and/or prevention of cancer, infectious diseases or a disease characterized by aberration of cellular energy metabolism, such as obesity.

In one aspect, the compounds of the disclosure are for use in the treatment and/or prevention of obesity.

In one aspect, the compounds of the disclosure are for use in the treatment and/or prevention of leukemia, non-small cell lung cancer, hepatocellular carcinoma, or glioblastomas.

In one aspect, the glioblastomas are giant cell glioblastoma or gliosarcoma.

In one aspect, the pharmaceutical composition comprising a compound of the disclosure as defined above, further comprises at least one other therapeutic agent, selected from the group consisting of: histone deacetylase inhibitors, retinoid receptor modulators, anti-proliferative/antineoplastic agents, cytostatic agents, agents which inhibit cancer cell invasion, inhibitors of growth factor function, anti-angiogenic agents, cell cycle inhibitors, proteasome inhibitors, HSP90 inhibitors, selective COX-2 inhibitors or a chemotherapeutic agent.

In one aspect, the disclosure relates to a method of treating a disease or disorder in a subject, comprising administering to the subject an effective amount of a compound of the disclosure, or a pharmaceutical composition thereof, that inhibits the activity or expression of KDM1.

In one aspect, the disclosure relates to a pharmaceutical composition in the form of tablets, capsules, oral preparations, powders, granules, pills, injectable or infusible liquid, solutions, suspensions, emulsions, suppositories, ointments, creams, lotions, gels, pastes, or transdermal delivery devices.

Another aspect of the disclosure is a process for the preparation of a compound of formula (I) as defined above, the process comprising the steps of:

(1) the preparation of a compound of formula A2 by reaction of a compound of formula A1 with a suitable azide and in the presence of a base;

(2) the reaction of a compound of formula A2 with an amide A3 and CuI (copper(I) iodide) in presence of a base to obtain a compound of formula A4; and (3) the deprotection of a compound of formula A4 to obtain a compound of formula (I), as represented in Scheme A below:

Scheme A

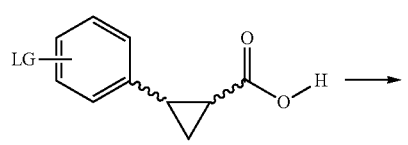

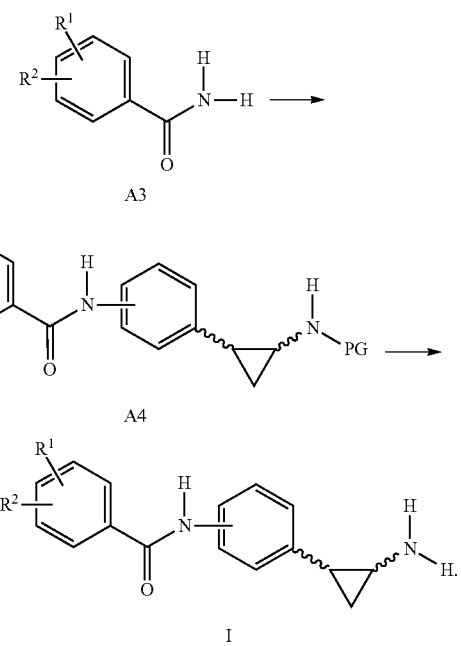

wherein $R^1$ and $R^2$ are as defined previously; and PG and LG are defined herein.

Another aspect of the disclosure is a process for preparing a compound of formula (I) as defined above, the process comprising the steps of:

(1) reacting a compound of formula B1 with compound of formula B2 in presence of a peptide coupling reagent, and (2) deprotecting a compound of formula B3 to obtain a compound of formula (I), as represented in Scheme B below:

Scheme B

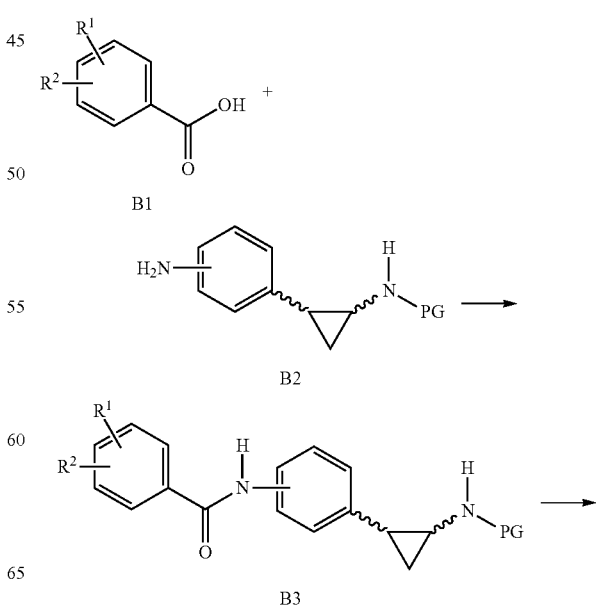

-continued

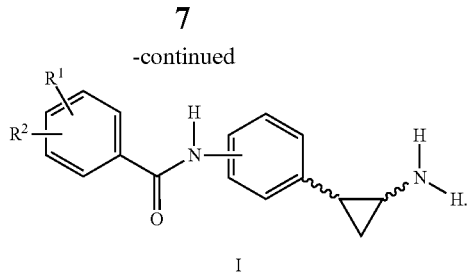

I wherein $R^1$, $R^2$, and PG are defined herein.

Another aspect of the disclosure is a kit comprising a compound as defined above and at least one therapeutic agent, preferably selected from the group consisting of: histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, Selective COX-2 inhibitors or a chemotherapeutic agent for use in the treatment and/or prevention of cancer, infectious diseases or a disease characterized by aberration of cellular energy metabolism, such as obesity.

Optionally, the compound of the disclosure and the at least one therapeutic agent are in separated containers.

The above description sets forth rather broadly the more important features of the present application in order that the detailed description thereof that follows may be understood, and in order that the present contributions to the art may be better appreciated. Other objects and features of the present application will become apparent from the following detailed description considered in conjunction with the examples.

DETAILED DESCRIPTION OF THE DISCLOSURE

Figure 1A:
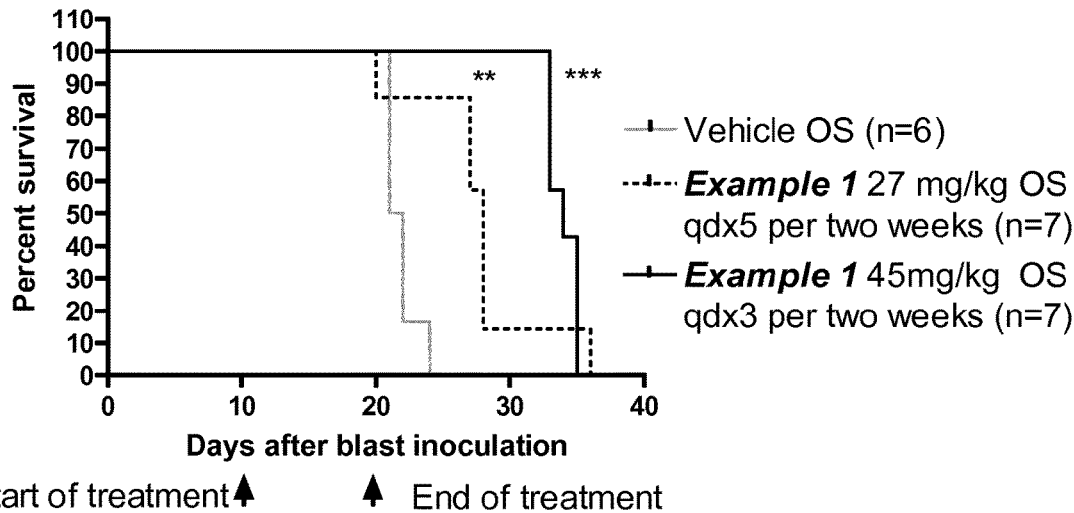
FIG. 1: A) In vivo efficacy experiment in an established murine promielocytic leukemia model of compound 1, N-[4-[trans-2-aminocyclopropyl]phenyl]-4-(4-methylpiperazin-1-yl)benzamide dihydrochloride (Example 1). Kaplan-Meier survival curves of leukemic mice treated with compound 1 and its respective vehicle. Treatment started once blast cells are detected in the recipients' peripheral blood (10 days after cell injection). Compound 1 was orally administered at the dose of 27 mg/kg for five days per week for two weeks and at the dose of 45 mg/kg for three days per week for two weeks. Increased survival of mice in the leukemia model is observed in the treated group. B): In vivo efficacy experiment in an established murine promielocytic leukemia model of compound 10, N-[4-[(1S,2R)-2-aminocyclopropyl]phenyl]-4-(4-methylpiperazin-1-yl)benzamide dihydrochloride. Kaplan-Meier survival curves of leukemic mice treated with compound 10 and its respective vehicle. Treatment started once blast cells are detected in the recipients' peripheral blood (10 days after cell injection). Compound 10 was orally administered at the doses of 11.25 and 22.5 mg/kg for three days per week for three weeks. Increased survival of mice in the leukemia model is observed in the treated group.

The details of one or more embodiments of the application are set forth in the accompanying description below. Although any methods and materials similar or equivalent to those described herein can be used in the practice or testing of the present application, the preferred methods and materials are now described. Other features, objects, and advantages of the application will be apparent from the description. In the specification, the singular forms also include the plural unless the context clearly dictates otherwise. Unless defined otherwise, all technical and scientific terms used herein have the same meaning as commonly understood by one of ordinary skill in the art to which this application belongs. In the case of conflict, the present specification will control.

The present disclosure relates to substituted cyclopropylamine compounds which may have highly potent activities of the KDM1A enzyme and/or of the KDM1B enzyme and low inhibitory activity of monoamine oxidases (MAOs).

In one aspect, the present disclosure relates to compounds which inhibit KDM1.

In one aspect, the present disclosure relates to compounds that inhibit KDM1A and/or KDM1B enzymes to a greater degree than MAOs.

In one aspect, the present disclosure relates to compounds for the prevention or therapy of diseases and conditions associated with the activity of the histone demethylases.

The present disclosure relates to compounds of general formula (I)

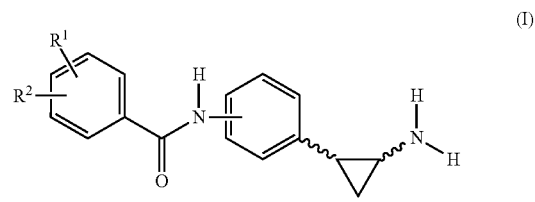

or a pharmaceutically acceptable salt, solvate, or prodrug thereof, wherein:

$R^1$ is heterocyclyl or heterocyclyl substituted by oxo, wherein the heterocyclyl is unsubstituted or substituted by one or more $C_1$-$C_6$ alkyl groups; and $R^2$ is hydrogen, halogen, $C_1$-$C_6$ alkyl, $C_1$-$C_6$ alkoxy, $C_1$-$C_6$ haloalkyl, or $C_1$-$C_6$ haloalkoxy, or benzyloxycarbonylamino.

In one aspect, $R^1$ is pyrrolidinyl, piperidinyl, piperazinyl, tetrahydrofuranyl, tetrahydropyranyl, morpholinyl, thiomorpholinyl, tetrahydroquinolinyl, tetrahydroisoquinolinyl, tetrahydroquinoxalinyl, benzodioxolyl, 2,3-dihydro-benzodioxinyl, benzoxazolyl, azepinyl, diazapinyl or 2-oxooxazolidinyl, wherein each is unsubstituted or substituted by one or more $C_1$-$C_6$ alkyl groups.

In one aspect, $R^1$ is 4-methylpiperazin-1-yl, 1-methylpiperidin-4-yl, piperidin-1-yl, or 2-oxooxazolidin-3-yl.

In one aspect, $R^1$ is heterocyclyl.

In one aspect, $R^1$ is heterocyclyl substituted by one or more $C_1$-$C_6$ alkyl groups.

In one aspect, $R^1$ is heterocyclyl substituted by oxo, and further substituted by one or more $C_1$-$C_6$ alkyl groups.

In one aspect, $R^1$ is unsubstituted heterocyclyl.

In one aspect $R^1$ is piperidinyl, piperazinyl, or 2-oxooxazolidinyl, wherein each is unsubstituted or substituted by one or more $C_1$-$C_6$ alkyl groups.

In one aspect $R^2$ is hydrogen.

In one aspect $R^2$ is benzyloxycarbonylamino.

In one aspect $R^2$ is halogen, $C_1$-$C_6$ alkyl, $C_1$-$C_6$ alkoxy, $C_1$-$C_6$ haloalkyl, or $C_1$-$C_6$ haloalkoxy.

In one aspect, $R^1$ is heterocyclyl and $R^2$ is hydrogen.

In one aspect, $R^1$ is heterocyclyl and $R^2$ is benzyloxycarbonylamino.

In one aspect, $R^1$ is heterocyclyl and $R^2$ is halogen, $C_1$-$C_6$ alkyl, $C_1$-$C_6$ alkoxy, $C_1$-$C_6$ haloalkyl, or $C_1$-$C_6$ haloalkoxy.

In one aspect, $R^1$ is heterocyclyl substituted by one or more $C_1$-$C_6$ alkyl groups and $R^2$ is hydrogen.

In one aspect, $R^1$ is heterocyclyl substituted by one or more $C_1$-$C_6$ alkyl groups and $R^2$ is benzyloxycarbonylamino.

In one aspect, $R^1$ is heterocyclyl substituted by one or more $C_1$-$C_6$ alkyl groups and $R^2$ is halogen, $C_1$-$C_6$ alkyl, $C_1$-$C_6$ alkoxy, $C_1$-$C_6$ haloalkyl, or $C_1$-$C_6$ haloalkoxy.

In one aspect, $R^1$ is heterocyclyl substituted by oxo, and further substituted by one or more $C_1$-$C_6$ alkyl groups, and $R^2$ is hydrogen.

In one aspect, $R^1$ is heterocyclyl substituted by oxo, and further substituted by one or more $C_1$-$C_6$ alkyl groups, and $R^2$ is benzyloxycarbonylamino.

In one aspect, $R^1$ is heterocyclyl substituted by oxo, and further substituted by one or more $C_1$-$C_6$ alkyl groups, and $R^2$ is halogen, $C_1$-$C_6$ alkyl, $C_1$-$C_6$ alkoxy, $C_1$-$C_6$ haloalkyl, or $C_1$-$C_6$ haloalkoxy.

In one aspect, $R^1$ is unsubstituted heterocyclyl and $R^2$ is hydrogen.

In one aspect, $R^1$ is unsubstituted heterocyclyl and $R^2$ is benzyloxycarbonylamino.

In one aspect, $R^1$ is unsubstituted heterocyclyl and $R^2$ is halogen, $C_1$-$C_6$ alkyl, $C_1$-$C_6$ alkoxy, $C_1$-$C_6$ haloalkyl, or $C_1$-$C_6$ haloalkoxy.

In one aspect, $R^1$ is piperidinyl, piperazinyl, or 2-oxooxazolidinyl, wherein each is unsubstituted or substituted by one or more $C_1$-$C_6$ alkyl groups, and $R^2$ is hydrogen.

In one aspect, $R^1$ is piperidinyl, piperazinyl, or 2-oxooxazolidinyl, wherein each is unsubstituted or substituted by one or more $C_1$-$C_6$ alkyl groups, and $R^2$ is benzyloxycarbonylamino.

In one aspect, $R^1$ is piperidinyl, piperazinyl, or 2-oxooxazolidinyl, wherein each is unsubstituted or substituted by one or more $C_1$-$C_6$ alkyl groups, and $R^2$ is halogen, $C_1$-$C_6$ alkyl, $C_1$-$C_6$ alkoxy, $C_1$-$C_6$ haloalkyl, or $C_1$-$C_6$ haloalkoxy.

In one aspect, $R^1$ is 4-methylpiperazin-1-yl and $R^2$ is hydrogen.

In one aspect, $R^1$ is 4-methylpiperazin-1-yl and $R^2$ is benzyloxycarbonylamino.

In one aspect, $R^1$ is 4-methylpiperazin-1-yl and $R^2$ is halogen, $C_1$-$C_6$ alkyl, $C_1$-$C_6$ alkoxy, $C_1$-$C_6$ haloalkyl, or $C_1$-$C_6$ haloalkoxy.

In one aspect, $R^1$ is 1-methylpiperidin-4-yl and $R^2$ is hydrogen.

In one aspect, $R^1$ is 1-methylpiperidin-4-yl and $R^2$ is benzyloxycarbonylamino.

In one aspect, $R^1$ is 1-methylpiperidin-4-yl and $R^2$ is halogen, $C_1$-$C_6$ alkyl, $C_1$-$C_6$ alkoxy, $C_1$-$C_6$ haloalkyl, or $C_1$-$C_6$ haloalkoxy.

In one aspect, $R^1$ is piperidin-1-yl and $R^2$ is hydrogen.

In one aspect, $R^1$ is piperidin-1-yl and $R^2$ is benzyloxycarbonylamino.

In one aspect, $R^1$ is piperidin-1-yl and $R^2$ is halogen, $C_1$-$C_6$ alkyl, $C_1$-$C_6$ alkoxy, $C_1$-$C_6$ haloalkyl, or $C_1$-$C_6$ haloalkoxy.

In one aspect, $R^1$ is 2-oxooxazolidin-3-yl and $R^2$ is hydrogen.

In one aspect, $R^1$ is 2-oxooxazolidin-3-yl and $R^2$ is benzyloxycarbonylamino.

In one aspect, $R^1$ is 2-oxooxazolidin-3-yl and $R^2$ is halogen, $C_1$-$C_6$ alkyl, $C_1$-$C_6$ alkoxy, $C_1$-$C_6$ haloalkyl, or $C_1$-$C_6$ haloalkoxy.

In one aspect, the compound of the disclosure is selected from:

N-[4-[trans-2-aminocyclopropyl]phenyl]-4-(4-methylpiperazin-1-yl)benzamide;

N-[4-[trans-2-aminocyclopropyl]phenyl]-4-(1-methyl-4-piperidyl)benzamide;

N-[4-[trans-2-aminocyclopropyl]phenyl]-3-(2-oxooxazolidin-3-yl)benzamide;

N-[4-[trans-2-aminocyclopropyl]phenyl]-4-morpholino-benzamide;

N-[4-[trans-2-aminocyclopropyl]phenyl]-4-(2-oxooxazolidin-3-yl)benzamide;

benzyl N-[5-[[4-[(trans-2-aminocyclopropyl]phenyl]carbamoyl]-2-(4-methylpiperazin-1-yl)phenyl]carbamate;

benzyl N-[4-[[4-[trans-2-aminocyclopropyl]phenyl]carbamoyl]-2-(4-methylpiperazin-1-yl)phenyl]carbamate;

benzyl N-[5-[[4-[trans-2-aminocyclopropyl]phenyl]carbamoyl]-2-(1-piperidyl)phenyl]carbamate;

benzyl N-[5-[[4-[trans-2-aminocyclopropyl]phenyl]carbamoyl]-2-morpholino-phenyl]carbamate;

N-[4-[(1S,2R)-2-aminocyclopropyl]phenyl]-4-(4-methylpiperazin-1-yl)benzamide;

N-[4-[(1S,2R)-2-aminocyclopropyl]phenyl]-3-(2-oxooxazolidin-3-yl)benzamide;

N-[4-[(1R,2S)-2-aminocyclopropyl]phenyl]-4-(4-methylpiperazin-1-yl)benzamide;

N-[4-[(1R,2S)-2-aminocyclopropyl]phenyl]-3-(2-oxooxazolidin-3-yl)benzamide; or a pharmaceutically acceptable salt, solvate, or prodrug thereof.

In one aspect, the disclosure relates to a pharmaceutical composition comprising a compound of the disclosure, or a pharmaceutically acceptable salt, solvate, or prodrug thereof and a pharmaceutically acceptable carrier and/or diluent.

In one aspect, the disclosure relates to a method of preventing or treating a disease or disorder comprising administering to a subject in need thereof an effective amount of a compound of the disclosure, or a pharmaceutically acceptable salt, solvate, or prodrug thereof, or a pharmaceutical composition of the disclosure.

In one aspect, the application relates to the use of a compound of the disclosure, or a pharmaceutically acceptable salt, solvate, or prodrug thereof, or a pharmaceutical composition of the disclosure for preventing or treating a disease or disorder in a subject in need thereof.

In one aspect, the disclosure relates to the use of a compound of the disclosure, or a pharmaceutically acceptable salt, solvate, or prodrug thereof, or a pharmaceutical composition of the disclosure in the manufacture of a medicament for preventing or treating a disease or disorder in a subject in need thereof.

In one aspect, the disclosure relates to a method of treating a disease or disorder in a subject, comprising administering to the subject an effective amount of a compound of the disclosure, or a pharmaceutical composition thereof, that inhibits the activity or expression of KDM1.

In one aspect, the compounds of the disclosure are for use in the treatment and/or prevention of cancer, infectious diseases or a disease characterized by aberration of cellular energy metabolism, such as obesity.

In one aspect, the compounds of the disclosure are useful in the treatment and/or prevention of cancer, wherein the cancer is selected from the group consisting of acute and chronic myeloid leukemia, acute and chronic lymphoblastic leukemia, myelodysplastic syndromes, multiple myeloma, Hodgkin's disease, non-Hodgkin's lymphomas, cutaneous and peripheral T-cell lymphoma, adult T-cell leukemia, large B-cell lymphoma; mammary tumors; pulmonary tumors and pleural mesotheliomas, adenocarcinoma, non-small lung cancer, small-cell lung cancer; skin tumors including basal cell carcinomas (basaliomas), melanomas, squamous cell carcinoma, Kaposi's sarcoma, keratocanthomas; osteosarcomas, fibrosarcomas, rhabdomyosarcomas, neuroblastomas, glioblastomas, cerebral tumors, head and neck cancer, testicular and ovarian tumors, cervical carcinoma, endometrial and prostate tumors (for example advanced prostate cancer), thyroid carcinomas (for example thyroid follicular cancer), colon cancers (for example colon adenocarcinoma, colon adenoma), gastric tumors and gastrointestinal adenocarcinomas, hepatocellular carcinomas, pancreatic carcinomas (for example exocrine pancreatic carcinoma), renal tumors, teratocarcinomas and embryonic carcinomas.

In one aspect, the compounds of the disclosure are for use in the treatment and/or prevention of leukemia, non-small cell lung cancer, hepatocellular carcinoma, or glioblastomas.

In one aspect, the glioblastomas are giant cell glioblastoma or gliosarcoma.

In one aspect, the compounds of the disclosure are useful in the treatment and/or prevention of infectious diseases.

In one aspect, the compounds of the disclosure are useful in the treatment and/or prevention a disease characterized by aberration of cellular energy metabolism In one aspect, the compounds of the disclosure are useful in the treatment and/or prevention of obesity.

In one aspect, the pharmaceutical composition comprising a compound of the disclosure as defined above, further comprises at least one other therapeutic agent, selected from the group consisting of: histone deacetylase inhibitors, retinoid receptor modulators, anti-proliferative/antineoplastic agents, cytostatic agents, agents which inhibit cancer cell invasion, inhibitors of growth factor function, anti-angiogenic agents, cell cycle inhibitors, proteasome inhibitors, HSP90 inhibitors, selective COX-2 inhibitors or a chemotherapeutic agent.

In one aspect, the disclosure relates to a pharmaceutical composition in the form of tablets, capsules, oral preparations, powders, granules, pills, injectable or infusible liquid, solutions, suspensions, emulsions, suppositories, ointments, creams, lotions, gels, pastes, or transdermal delivery devices.

In one aspect, the compound of the application or composition is administered orally, parenterally, subcutaneously, intravenously, intramuscularly, intraperitoneally, by intranasal instillation, by intracavitary or intravesical instillation, topically, intraarterially, intralesionally, by metering pump, or by application to mucous membranes. In another aspect, the compound of the application or composition is administered orally, parenterally, or intravenously.

In one aspect, the compound of the application or composition is administered orally.

In one aspect, the compound of the application or composition is administered parenterally.

In one aspect, the compound of the application or composition is administered intravenously.

In one aspect, the disclosure related to a process for the preparation of a compound of formula (I), or a pharmaceutically acceptable salt, solvate, or prodrug thereof, as defined above, the process comprising the steps of:

(1) the preparation of a compound of formula A2 by reaction of a compound of formula A1 with a suitable azide and in the presence of a base;

(2) the reaction of a compound of formula A2 with an amide A3 and CuI (copper(I) iodide) in presence of a base to obtain a compound of formula A4; and (3) the deprotection of a compound of formula A4 to obtain a compound of formula (I), as represented in Scheme A below:

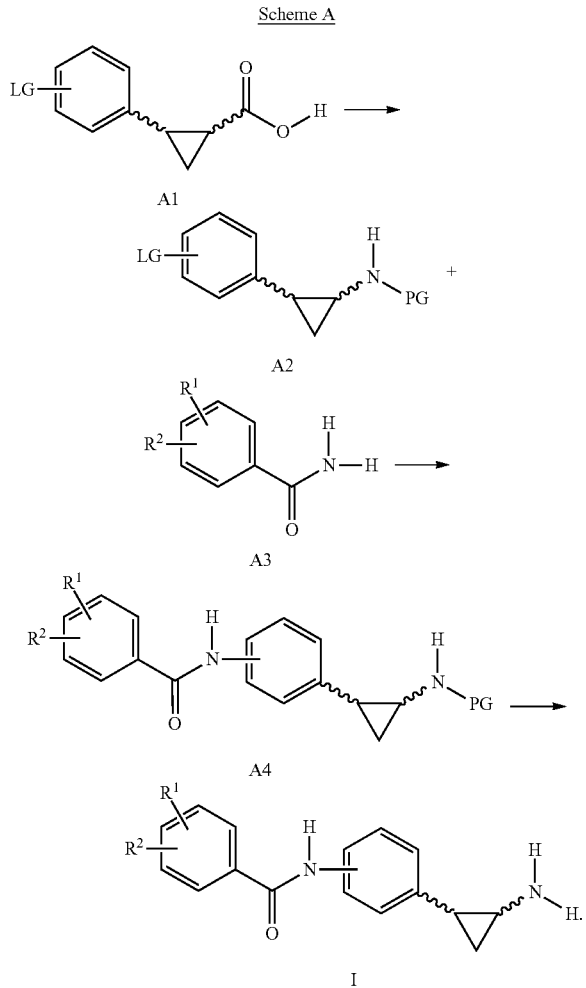

wherein $R^1$ and $R^2$ are as defined previously;

PG is a protecting group chosen among those known in the art; and

LG s a protecting group chosen among those known in the art.

In one aspect PG is selected from the group consisting of carboxybenzyl, tert-butyloxycarbonyl (BOC), and 9-fluorenylmethyloxycarbonyl.

In one aspect, LG is selected from the group consisting of bromide, iodide, and chloride.

Another aspect of the disclosure is a process for preparing a compound of formula (I), or a pharmaceutically acceptable salt, solvate, or prodrug thereof, as defined above, the process comprising the steps of:

(1) reacting a compound of formula B1 with compound of formula B2 in presence of a peptide coupling reagent, and (2) deprotecting a compound of formula B3 to obtain a compound of formula (I), as represented in Scheme B below:

Scheme B

B1

B2

B3

I wherein $R^1$ and $R^2$ are as defined previously;

PG is a protecting group chosen among those known in the art; and

LG s a protecting group chosen among those known in the art.

In one aspect PG is selected from the group consisting of carboxybenzyl, tert-butyloxycarbonyl (BOC), and 9-fluorenylmethyloxycarbonyl.

In one aspect, LG is selected from the group consisting of bromide, iodide, and chloride.

Another aspect of the disclosure is a kit comprising a compound of formula (I) as defined above and at least one therapeutic agent, preferably selected from the group consisting of: histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, Selective COX-2 inhibitors or a chemotherapeutic agent for use in the treatment and/or prevention of cancer, infectious diseases or a disease characterized by aberration of cellular energy metabolism, such as obesity. Optionally, the compound of the disclosure and the at least one therapeutic agent are in separated containers.

The above description sets forth rather broadly the more important features of the present application in order that the detailed description thereof that follows may be understood, and in order that the present contributions to the art may be better appreciated. Other objects and features of the present application will become apparent from the following detailed description considered in conjunction with the examples.

Preparation of Compounds of the Disclosure

Compounds of general formula (I) may be prepared according to Scheme A:

Scheme A

A1

A2

A3

A4

I wherein $R^1$ and $R^2$ are as defined above for formula (I), PG is a protecting group chosen among those known in the art, for example carboxybenzyl, tert-butyloxycarbonyl (BOC), 9-fluorenylmethyloxycarbonyl, etc. and LG is a leaving group, for example bromide, iodide or chloride.

Compounds of formula A1 and A3 are known compounds or may be prepared by known methods. For example, cyclopropyl carboxylate compounds A1 may be obtained following the procedures described by starting from known epoxides and phosphoranes (Denney et al. J. Am. Chem. Soc. 1959, 6330-6331).

The carboxylic acid of formula A1 may be converted into the protected amine of formula A2 by reaction with a suitable azide, such as diphenyl phosphoryl azide, in the presence of a suitable base (e.g. triethylamine) and in a suitable solvent such as tert-butanol at a temperature ranging from room temperature to the boiling point of the solvent.

A compound of formula A4, may be prepared according to the Ullmann type reaction by reacting a compound of formula A2 and a compound of formula A3 with CuI (copper(I) iodide) in presence of a suitable base, such as $Cs_2CO_3$, $K_2CO_3$, triethylamine, N,N'-dimethylethane-1,2-diamine, N,N'-dimethylcyclohexane-1,2-diamine or 2-aminoethanol, and in a suitable solvent, for example in dimethylacetamide, tetrahydrofuran or dioxane, at a temperature ranging from room temperature to the boiling point of the solvent.

A compound of formula A4 may be deprotected to obtain a compound of formula (I) according to known methods, e.g. by treatment of the BOC derivative with HCl or TFA (trifluoroacetic acid) in a suitable solvent such as dioxane, $Et_2O$ or dichloromethane, at a temperature ranging from 0° C. to room temperature.

The title compounds of Examples 1-5 were synthesized according to Scheme A, and are listed in Table 1.

TABLE 1

| Example No. | Compound Name | Compound Structure |
|---|---|---|
| 1 | N-[4-[trans-2-aminocyclopropyl]phenyl]-4-(4-methylpiperazin-1-yl)benzamide dihydrochloride | 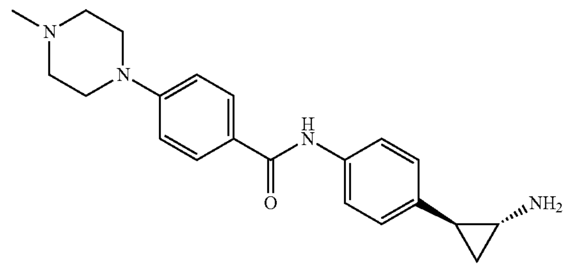 |
| 2 | N-[4-[trans-2-aminocyclopropyl]phenyl]-4-(1-methyl-4-piperidyl)benzamide hydrochloride | 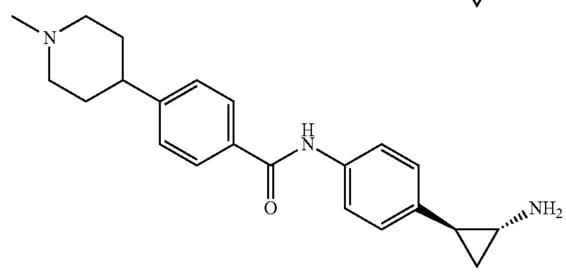 |
| 3 | N-[4-[trans-2-aminocyclopropyl]phenyl]-3-(2-oxooxazolidin-3-yl)benzamide hydrochloride | 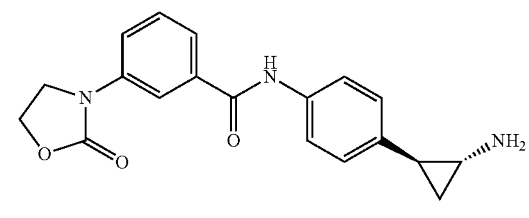 [SMILES: N[C@@H]1C[C@H]1c1ccc(NC(=O)c2cccc(N3CCOC3=O)c2)cc1] |
| 4 | N-[4-[trans-2-aminocyclopropyl]phenyl]-4-morpholino-benzamide hydrochloride | 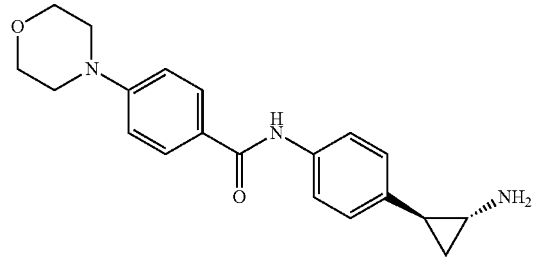 [SMILES: N[C@@H]1C[C@H]1c1ccc(NC(=O)c2ccc(N3CCOCC3)cc2)cc1] |
| 5 | N-[4-[trans-2-aminocyclopropyl]phenyl]-4-(2-oxooxazolidin-3-yl)benzamide hydrochloride | 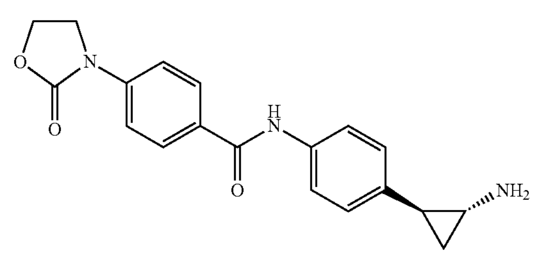 [SMILES: N[C@@H]1C[C@H]1c1ccc(NC(=O)c2ccc(N3CCOC3=O)cc2)cc1] |

Alternatively, compounds of general formula (I) may be prepared according to Scheme B:

Scheme B

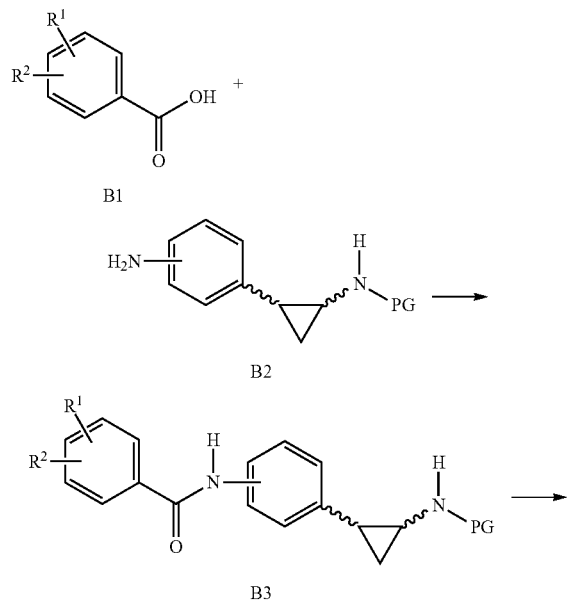

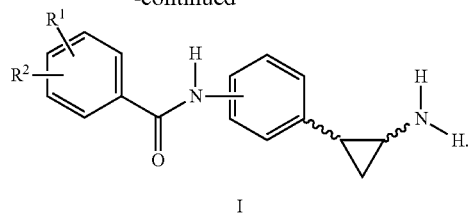

wherein $R^1$, $R^2$ and PG are as defined above.

The reaction of a compound of formula B1 with a compound of formula B2 can be carried out with peptide coupling reagents such as PyBOP (benzotriazol-1-yl-oxytripyrrolidinophosphonium hexafluorophosphate) or EDC (1-(3-dimethylaminopropyl)-3-ethylcarbodiimide), optionally in the presence of a suitable base (e.g. triethylamine or di-isopropylethylamine) in a suitable solvent (e.g. tetrahydrofuran, dichloromethane or DMF). Generally an activator of the condensation reaction, such as HOBt (1-hydroxybenzotriazole) or HOAt (1-hydroxy-7-aza-benzotriazole), can be added to the reaction mixture. The reaction can be carried out at room temperature for a period lasting between about 2 and 24 h. A compound of formula B3 may be deprotected to obtain a compound of formula (I) according to known methods, e.g. by treatment of a BOC derivative with HCl or TFA (trifluoroacetic acid) in a suitable solvent such as dioxane, $Et_2O$ or dichloromethane, at a temperature ranging from 0° C. to room temperature.

The title compounds of Examples 6-9 were synthesized according to Scheme B, and are listed in Table 2.

TABLE 2

| Example No. | Compound Name | Compound Structure |
|---|---|---|
| 6 | Benzyl N-[4-[[4-[trans-2-aminocyclopropyl]phenyl]carbamoyl]-2-(4-methylpiperazin-1-yl)phenyl]carbamate dihydrochloride | 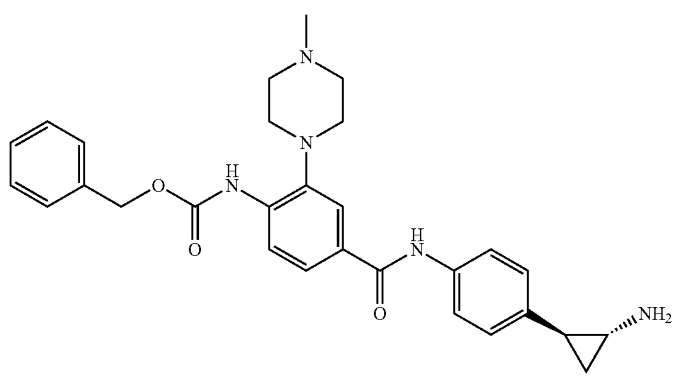 [SMILES: CN1CCN(c2cc(C(=O)Nc3ccc([C@@H]4C[C@H]4N)cc3)ccc2NC(=O)OCc2ccccc2)CC1] |
| 7 | Benzyl N-[5-[[4-[(trans-2-aminocyclopropyl]phenyl]carbamoyl]-2-(4-methylpiperazin-1-yl)phenyl]carbamate dihydrochloride | 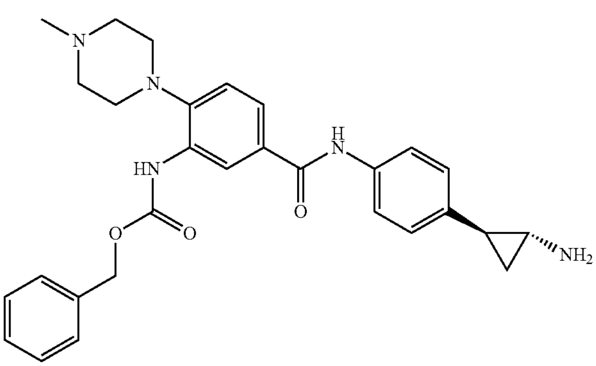 [SMILES: CN1CCN(c2ccc(C(=O)Nc3ccc([C@@H]4C[C@H]4N)cc3)cc2NC(=O)OCc2ccccc2)CC1] |

TABLE 2-continued

| Example No. | Compound Name | Compound Structure |
| --- | --- | --- |
| 8 | Benzyl N-[5-[[4-[trans-2-aminocyclopropyl]phenyl]carbamoyl]-2-(1-piperidyl)phenyl]carbamate hydrochloride | 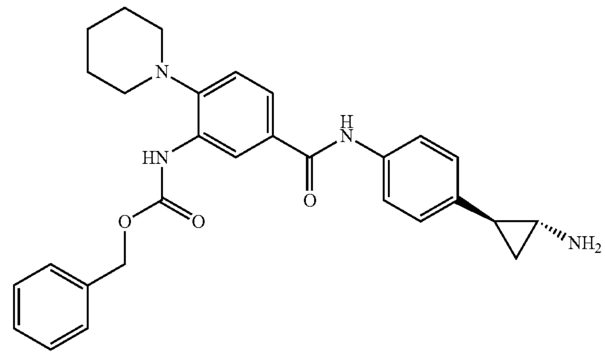 |
| 9 | Benzyl N-[5-[[4-[trans-2-aminocyclopropyl]phenyl]carbamoyl]-2-morpholino-phenyl]carbamate hydrochloride | 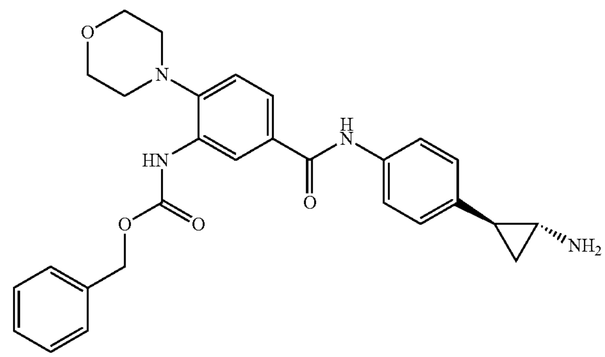 |

Compounds of formula B2 are known compounds (J. Am. Chem. Soc. 2010, 132, 6827-6833, GB2404658) or may be prepared by known methods.

Compounds of formula B1 are known compounds or may be prepared by known methods. In case, wherein $R^1$ is morpholinyl, 4-methylpiperazin-1-yl, or piperidin-1-yl and $R^2$ is benzyloxycarbonylamino, compounds of formula B1 can be prepared according to the following Scheme C:

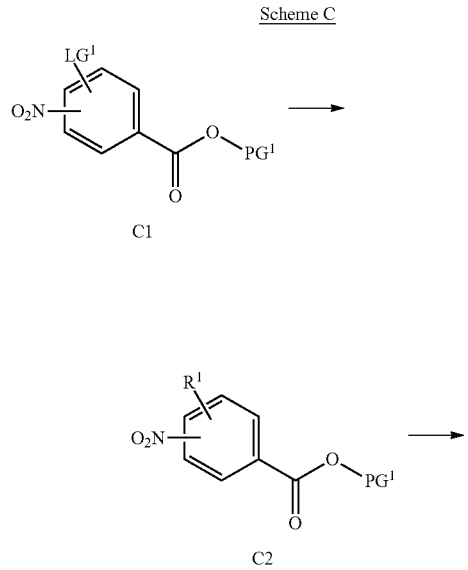

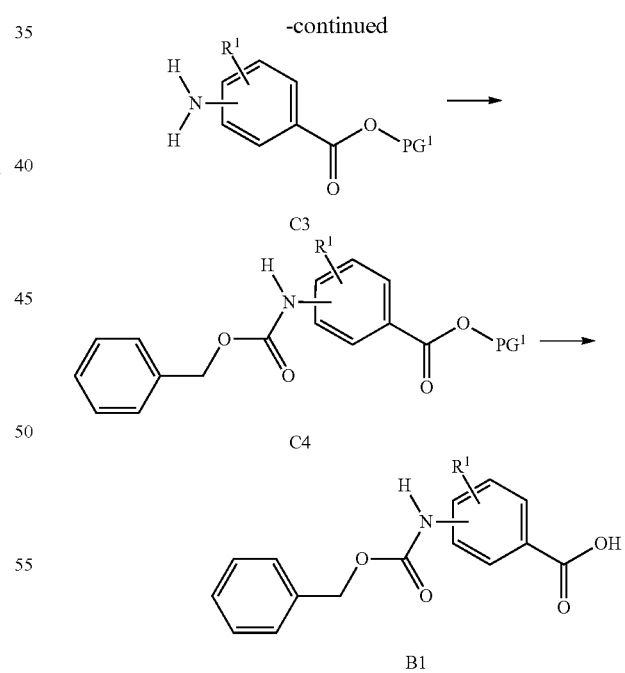

wherein $PG^1$ is a protecting group chosen among those known in the art, for example methyl, tert-butyl, etc., and $LG^1$ is a leaving group, for example fluoride or chloride.

Compounds of formula C1 are known compounds or may be prepared by known methods.

Compounds of formula C1 can be converted into compound of formula C2 by reaction with morpholine, 4-methylpiperazine, or piperidine in presence of a base (e.g. K₂CO₃) in a suitable solvent (e.g. tetrahydrofuran, dichloromethane or DMF). Reduction of the nitro derivative C2 to the amine analogue of formula C3 can be achieved by conventional catalytic hydrogenation, e.g. in a Parr or H-Cube apparatus using a palladium or platinum catalyst. The compound of formula C3 can then be converted into a compound of formula C4 by reaction with benzyl chloroformate in presence of a suitable base, such as triethylamine, in a suitable solvent, for example in tetrahydrofuran or dioxane, at a temperature ranging from 0° C. to room temperature. A compound of formula C4 may be deprotected to obtain a compound of formula B1 according to known methods, e.g. by treatment of a tert-butyl derivative with HCl or TFA (trifluoroacetic acid) in a suitable solvent such as dioxane, THF, Et₂O or dichloromethane, at a temperature ranging from 0° C. to room temperature.

The title compounds of Examples 10 and 11 (Table 3) were synthesized from (1R,2R)-2-(4-iodophenyl)cyclopropanecarboxylic acid (Intermediate 3) and Examples 12 and 13 (Table 3) starting from (1S,2S)-2-(4-iodophenyl)cyclopropanecarboxylic acid (Intermediate 4), according to the procedure described for Example 1.

TABLE 3

| Example No. | Compound Name | Compound Structure |
|---|---|---|
| 10 | N-[4-[(1S,2R)-2-aminocyclopropyl]phenyl]-4-(4-methylpiperazin-1-yl)benzamide dihydrochloride | 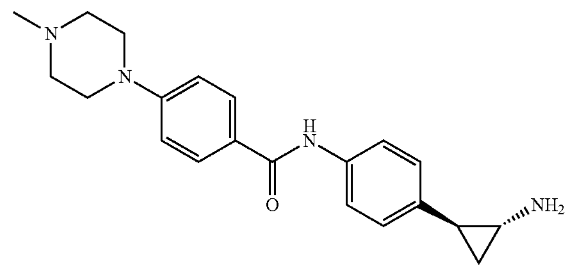 |
| 11 | N-[4-[(1S,2R)-2-aminocyclopropyl]phenyl]-3-(2-oxooxazolidin-3-yl)benzamide hydrochloride | 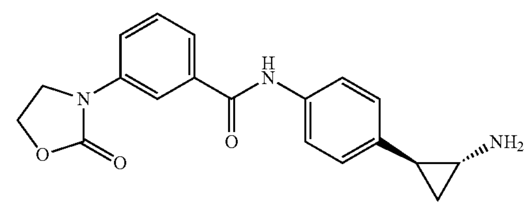 [SMILES: N[C@@H]1C[C@H]1c1ccc(NC(=O)c2cccc(N3CCOC3=O)c2)cc1] |
| 12 | N-[4-[(1R,2S)-2-aminocyclopropyl]phenyl]-4-(4-methylpiperazin-1-yl)benzamide dihydrochloride | 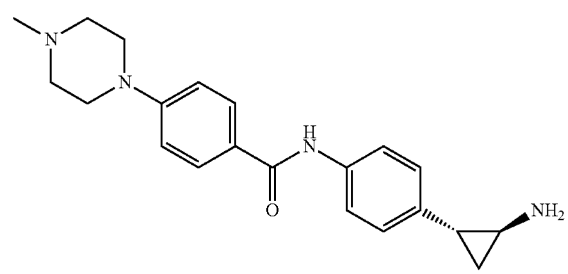 [SMILES: CN1CCN(c2ccc(C(=O)Nc3ccc([C@H]4C[C@@H]4N)cc3)cc2)CC1] |
| 13 | N-[4-[(1R,2S)-2-aminocyclopropyl]phenyl]-3-(2-oxooxazolidin-3-yl)benzamide hydrochloride | 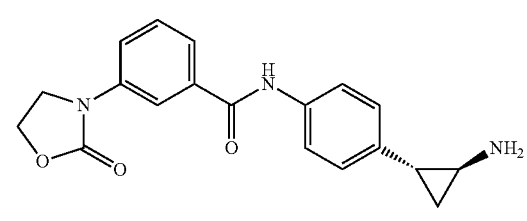 [SMILES: N[C@H]1C[C@@H]1c1ccc(NC(=O)c2cccc(N3CCOC3=O)c2)cc1] |

As described herein, the preparation of the compounds of the disclosure entailed the synthesis of various intermediate compounds. These include the compounds listed below in Table 4.

TABLE 4

Intermediate Compounds.

| Molecular structure | Recrystallization Solvent, where necessary | m.p. (° C.) | Yield (%) |
|---|---|---|---|
| 3-(2-oxooxazolidin-3-yl)benzamide | | nd | nd |
| 4-(2-oxooxazolidin-3-yl)benzamide | | nd | nd |
| trans-2-(4-iodophenyl)cyclopropane-1-carboxylic acid | | nd | nd |
| trans-2-(4-iodophenyl)cyclopropane-1-carboxylic acid (enantiomer) | | nd | nd |
| tert-butyl 3-nitro-4-(piperidin-1-yl)benzoate | toluene | 144-146 | 88 |
| tert-butyl 4-morpholino-3-nitrobenzoate | toluene | 149-151 | 85 |
| tert-butyl 4-(4-methylpiperazin-1-yl)-3-nitrobenzoate | toluene | 138-140 | 92 |

TABLE 4-continued
Intermediate Compounds.
| Molecular structure | Recrystallization Solvent, where necessary | m.p. (° C.) | Yield (%) |
|---|---|---|---|
| 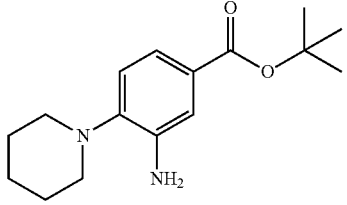 | cyclohexane | 115-117 | 67 |
| 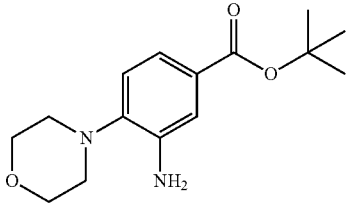 | cyclohexane | 126-128 | 73 |
| 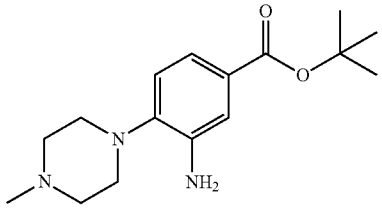 [SMILES: CN1CCN(c2ccc(C(=O)OC(C)(C)C)cc2N)CC1] | cyclohexane | 114-116 | 65 |
| 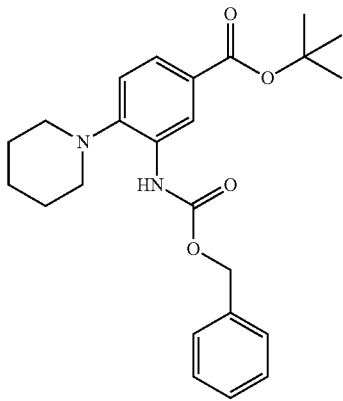 [SMILES: CC(C)(C)OC(=O)c1ccc(N2CCCCC2)c(NC(=O)OCc2ccccc2)c1] | — | oil | 68 |
| 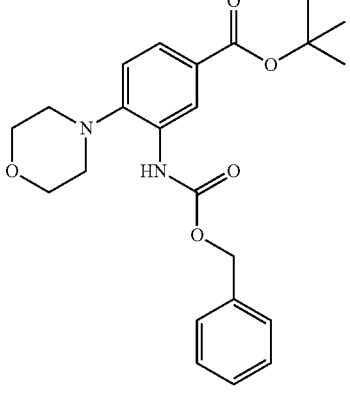 | — | oil | 71 |

TABLE 4-continued

Intermediate Compounds.

| Molecular structure | Recrystallization Solvent, where necessary | m.p. (° C.) | Yield (%) |
|---|---|---|---|
| (structure: 4-(4-methylpiperazin-1-yl)-3-(benzyloxycarbonylamino)benzoic acid tert-butyl ester) | — | oil | 65 |
| (structure: 3-(4-methylpiperazin-1-yl)-4-(benzyloxycarbonylamino)benzoic acid tert-butyl ester) | — | oil | 72 |
| (structure: 4-(piperidin-1-yl)-3-(benzyloxycarbonylamino)benzoic acid) | acetonitrile | 214-216 | 86 |
| (structure: 4-(morpholin-4-yl)-3-(benzyloxycarbonylamino)benzoic acid) | acetonitrile | 234-236 | 83 |

TABLE 4-continued

Intermediate Compounds.

| Molecular structure | Recrystallization Solvent, where necessary | m.p. (° C.) | Yield (%) |
|---|---|---|---|
| (structure: 4-(4-methylpiperazin-1-yl)-3-(benzyloxycarbonylamino)benzoic acid) | acetonitrile | 205-207 | 76 |
| (structure: N-(4-(2-(tert-butoxycarbonylamino)cyclopropyl)phenyl)-4-(piperidin-1-yl)-3-(benzyloxycarbonylamino)benzamide) | cyclohexane | 116-118 | 72 |
| (structure: N-(4-(2-(tert-butoxycarbonylamino)cyclopropyl)phenyl)-4-(morpholin-4-yl)-3-(benzyloxycarbonylamino)benzamide) | cyclohexane | 118-120 | 75 |

TABLE 4-continued

Intermediate Compounds.

| Molecular structure | Recrystallization Solvent, where necessary | m.p. (° C.) | Yield (%) |
|---|---|---|---|
| 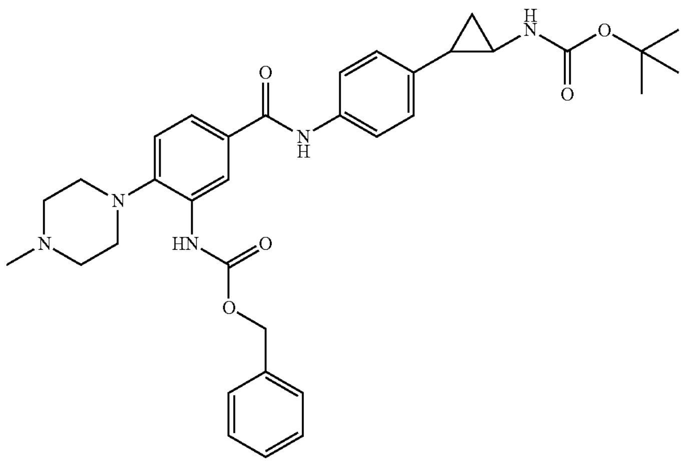 [SMILES: CN1CCN(c2ccc(C(=O)Nc3ccc(C4CC4NC(=O)OC(C)(C)C)cc3)cc2NC(=O)OCc2ccccc2)CC1] | cyclohexane | 125-127 | 68 |

(nd = not determined)

Biological Testing

The bioactivity of the compounds of this disclosure can be assessed in several assays, including those know in the art. These assays include: determination of the compounds' enzyme inhibitory effect on KDM1A (LSD1) activity (Forneris, F. et al. Trends Biochem. Sci. 2008, 33, 181-189; Forneris, F. et al. J. Biol. Chem. 2007, 282, 20070-20074); determination of the compounds' $IC_{50}$ values in human leukemia cells, i.e., MV4-11 cells; determination of the compounds' inhibitory effect on MAO-A and MAO-B activity (Binda, C. et al. Proc. Natl. Acad. Sci. USA, 2003, 9750-9755); verification of the compounds' inhibitory effect on KDM1A activity in cells (Harris, W J et al. Cancer Cell. 2012, 21, 473-487); assessment of the compounds' anticlonogenic potential on human THP-1 cells; assessment of the compounds' in vivo activity in a mouse model, wherein the mouse develops leukemia, and the model represents acute promyelocytic leukemia (Minucci, S. et al. Blood 2002, 100, 2989-2995); and an in vivo target modulation assay in mice to verify the compounds' ability to inhibit KDM1A (Saleque, S. et al. Mol. Cell, 27 (2007), pp. 562-572).

Definitions

In the present disclosure, "Heterocyclyl" represents a mono or bicyclic saturated or partially saturated non-aromatic ring system of, respectively, 4 to 12 members, which contains one, two, or three heteroatoms selected from nitrogen, oxygen, and sulfur and three to eleven carbon atoms. Examples of such heterocycles include, but are not limited to: pyrrolidinyl, piperidinyl, piperazinyl, tetrahydrofuranyl, tetrahydropyranyl, morpholinyl, thiomorpholinyl, tetrahydroquinolinyl, tetrahydroisoquinolinyl, tetrahydroquinoxalinyl, benzodioxolyl, 2,3-dihydro-benzodioxinyl, benzoxazolyl, azepinyl, and diazapinyl. "Heterocyclyl substituted by oxo" represents a mono or bicyclic saturated or partially saturated non-aromatic ring system of, respectively, 4 to 12 members, which contains one, two, or three heteroatoms selected from nitrogen, oxygen, and sulfur, and which is substituted by an oxo group. Examples include, but are not limited to 2-oxooxazolidin-3-yl.

The term "halogen" refers to fluoro, chloro, bromo, or iodo.

The term "$C_1$-$C_6$ alkyl" refers to a straight or branched hydrocarbon chain radical, consisting solely of carbon and hydrogen atoms, having from one to six carbon atoms. Suitable examples of $C_1$-$C_6$ alkyl include methyl, ethyl, n-propyl, isopropyl, butyl, tert-butyl, pentyl, and hexyl.

The term "$C_1$-$C_6$ alkoxy" refers to a straight or branched O—$C_1$-$C_6$ alkyl, where alkyl is as defined herein. The "$C_1$-$C_6$ alkoxy" group is preferably a linear or branched $C_1$-$C_4$ alkoxy group, more preferably a $C_1$-$C_2$ alkoxy group.

The term "$C_1$-$C_6$ haloalkyl" refers to a straight or branched hydrocarbon chain radical, which is substituted by one or more halogen atoms and having from one to six carbon atoms. The "$C_1$-$C_6$ haloalkyl" group is preferably a linear or branched $C_1$-$C_4$ haloalkyl group, more preferably a $C_1$-$C_2$ haloalkyl group, being in particular $CF_3$.

The term "$C_1$-$C_6$ haloalkoxy" refers to a straight or branched O—$C_1$-$C_6$ haloalkyl, where haloalkyl is as defined herein. The "$C_1$-$C_6$ haloalkoxy" group is preferably a linear or branched $C_1$-$C_4$ haloalkoxy group, more preferably a $C_1$-$C_2$ haloalkoxy group, being in particular $OCF_3$, $OCHF_2$ or $OCH_2F$.

In the case it is necessary to protect a chemical group of a compound of the present disclosure and/or an intermediate thereof, before carrying out one of the aforedescribed reactions, said chemical group can be protected and deprotected according to known methods. A thorough discussion for protection/deprotection steps is provided for example in Greene and Wuts (Greene, T. W.; Wuts, P. G. M. "Protective Groups in Organic Synthesis", John Wiley & Sons Inc., 2006) or in Kocienski (Kocienski, P. J. "Protecting Groups", George Thieme Verlag, 2005).

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent.

Compounds of Formula (I) where the combinations of $R^1$ and $R^2$ are not explicitly disclosed herein are permissable, but only if such combinations result in stable compounds.

Salification of the compounds of formula (I), and preparation of compounds of formula (I), free of their salts, can be carried out by known conventional methods.

Pharmaceutically acceptable salts comprise conventional non-toxic salts obtained by salification of a compound of formula (I) with inorganic acids (e.g. hydrochloric, hydrobromic, sulfuric, or phosphoric acids), or with organic acids (e.g. acetic, propionic, succinic, benzoic, sulfanilic, 2-acetoxy-benzoic, cinnamic, mandelic, salicylic, glycolic, lactic, oxalic, malic, maleic, malonic, fumaric, tartaric, citric, p-toluenesulfonic, methanesulfonic, ethanesulfonic, or naphthalensulfonic acids). For reviews on suitable pharmaceutical salts see Berge S. M. et al., J. Pharm. Sci. 1977, 66, 1-19; Gould P. L. Int. J. Pharm 1986, 33, 201-217; and Bighley et al. Encyclopedia of Pharmaceutical Technology, Marcel Dekker Inc., New York 1996, Volume 13, page 453-497. Other salts, which are not pharmaceutically acceptable, for example the trifluoroacetate salt, may be useful in the preparation of compounds of this disclosure and these form a further aspect of the disclosure. The disclosure includes within its scope all possible stoichiometric and non-stoichiometric forms of the salts of the compounds of formula (I).

In addition, the compounds of formula (I) may exist in unsolvated as well as in solvated forms with pharmaceutically acceptable solvents such as water, EtOH and the like.

Certain compounds of formula (I) may exist in stereoisomeric forms (e.g. they may contain one or more asymmetric carbon atoms). The individual stereoisomers (enantiomers and diastereomers) and mixtures of these are included within the scope of the present disclosure. The present disclosure also covers the individual isomers of the compounds represented by formula (I) as mixtures with isomers thereof in which one or more chiral centres are inverted.

The disclosure also includes all suitable isotopic variations of a compound of the disclosure. Examples of isotopes that can be incorporated into compounds of the disclosure include isotopes such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the disclosure, for example, those in which a radioactive isotope such as $^3H$ or $^{14}C$ is incorporated, are useful in drug and/or substrate tissue distribution studies. Further, substitution with isotopes such as deuterium $^2H$, may afford certain therapeutic advantages resulting from greater metabolic stability. Isotopic variations of the compounds of the disclosure can generally be prepared by conventional procedures such as by the illustrative methods or by the preparations described in the examples hereafter using appropriate isotopic variations of suitable reagents.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, it should be understood that the order of steps or order for performing certain actions are immaterial so long as the application remains operable. Moreover, two or more steps or actions may be conducted simultaneously.

In view of the above described mechanisms of action for the compounds of the disclosure, these compounds are useful in the prevention or treatment of tumor type diseases, including but not limited to: acute and chronic myeloid leukemia, acute and chronic lymphoblastic leukemia, myelodysplastic syndromes, multiple myeloma, Hodgkin's disease, non-Hodgkin's lymphomas, cutaneous and peripheral T-cell lymphoma, adult T-cell leukemia, large B-cell lymphoma; mammary tumors; pulmonary tumors and pleural mesotheliomas, adenocarcinoma, non-small lung cancer, small-cell lung cancer; skin tumors including basal cell carcinomas (basaliomas), melanomas, squamous cell carcinoma, Kaposi's sarcoma, keratocanthomas; osteosarcomas, fibrosarcomas, rhabdomyosarcomas, neuroblastomas, glioblastomas, cerebral tumors, head and neck cancer, testicular and ovarian tumors, cervical carcinoma, endometrial and prostate tumors (for example advanced prostate cancer), thyroid carcinomas (for example thyroid follicular cancer), colon cancers (for example colon adenocarcinoma, colon adenoma), gastric tumors and gastrointestinal adenocarcinomas, hepatocellular carcinomas, pancreatic carcinomas (for example exocrine pancreatic carcinoma), renal tumors, teratocarcinomas and embryonic carcinomas.

The compounds of the disclosure are also useful in the prevention or treatment of infections, including, but not limited to, infections caused by protozoa, fungi, phytotoxic agents, viruses and parasites, for example HIV or herpes virus infections.

Considering the role of KDM1A in the regulation of cellular energy expenditure in the adipocytes as well as the direct relation between KDM1A function and its target genes in adipose tissue of high fat diet mice, the compounds of the disclosure are also useful in the prevention or treatment of diseases characterized by aberration of cellular energy metabolism, such as obesity (Hino S. et al. Nat Commun. 2012, doi: 10.1038/ncomms1755).

Combination therapy" (or "co-therapy") includes the administration of a compound of the application and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present application.

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The compounds of formula (I) can also be used in combination with additional agents, in particular anti-tumor and differentiating agents, either by separate administrations, or by including the two active principles in the same pharmaceutical formulation. Non-exhaustive examples of suitable additional agents include:

a) histone deacetylase inhibitors (for example, but not limited to SAHA, PXD101, JNJ-26481585, SB939, ITF-2357, LBH589, PCI-24781, valproic acid, butyric acid, MS-275, MGCD0103 and FK-228);

b) retinoid receptor modulators such as 13-cis-retinoic acid, 9-cis-retinoic acid, bexarotene, alitretinoin, or tretinoin; vitamin D;

c) antiproliferative/antineoplastic drugs and combinations thereof, as used in medical oncology, such as alkylating agents (for example platin compounds like cis-platin, carboplatin, oxaliplatin, lobaplatin, satraplatin, nedaplatin, heptaplatin; nitrogen mustard such as chlorambucil, melphalan, chlormethine, cyclophosphamide, ifosfamide, trofosfamide, uramustine, bendamustine, estramustine; busulphan, temozolomide or nitrosoureas); antimetabolites (for example antifolates such as aminopterin, methotrexate, pemetrexed, raltitrexed); purines such as cladribine, clofarabine, fludarabine, mercaptopurine, pentostatin, thioguanine; pyrimidines like capecitabine, cytarabine, fluorouracil, floxuridine, gemcitabine; azacitidine, decitabine; cytosine arabinoside or hydroxyurea; antitumour antibiotics (for example anthracyclines like aclarubicin, amrubicin, daunomycin, doxorubicin, epirubicin, idarubicin, valrubicin, zorubicine; mitoxantrone; or antibiotics from streptomyces like actinomycin, bleomycin, mitomycin, or plicamycin); antimitotic agents (for example vinca alkaloids like vincristine, vinblastine, vindesine or vinorelbine; taxoids like docetaxel, paclitaxel or tesetaxel; epothilones like ixabepilone) and topoisomerase inhibitors (for example epipodophyllotoxins like etoposide and teniposide; amsacrine, camptothecin, irinotecan, rubitecan, and topotecan);

d) cytostatic agents such as antioestrogens (for example tamoxifen, toremifene, raloxifene, droloxifene and idoxifene), oestrogen receptor down regulators (for example fulvestrant), antiandrogens (for example bicalutamide, flutamide, nilutamide, liarozole or cyproterone acetate), LHRH antagonists or LHRH agonists (for example goserelin, leuprorelin or buserelin), progestogens (for example megestrol acetate), aromatase inhibitors (for example as anastrozole, letrozole, vorazole and exemestane) and inhibitors of 5-alpha-reductase such as finasteride;

e) agents which inhibit cancer cell invasion (for example metalloproteinase inhibitors and inhibitors of urokinase plasminogen activator receptor function);

f) inhibitors of growth factor function, for example growth factor antibodies, growth factor receptor antibodies (for example the anti-erbb2 antibody trastuzumab, the anti-erbb1 antibody cetuximab and panitumumab, the anti IGF1R antibody figitumumab), farnesyl transferase inhibitors, MEK inhibitors, tyrosine kinase inhibitors and serine/threonine kinase inhibitors, for example enzastaurin, dasatinib, erlotinib, gefitinib, imatinib, lapatinib, nilotinib, sorafenib, sunitinib, everolimus, sirolimus or temsirolimus;

g) antiangiogenic agents such as those which inhibit the effects of vascular endothelial growth factor, for example the anti-vascular endothelial cell growth factor antibody bevacizumab, lenalidomide or thalidomide;

h) cell cycle inhibitors including for example CDK inhibitors (for example but not limited to flavopiridol, roscovitine) and other inhibitors of cell cycle checkpoints; inhibitors of aurora kinase and other kinases involved in mitosis and cytokinesis regulation;

i) proteasome inhibitors (for example lactacystin, bortezomib, epoxomicin);

j) HSP90 inhibitors (for example but not limited to AT-13387, KOS-953, KOS-1022, CNF-1010, CNF-2024, SNX 5422, STA-9090, NVP-HSP990, NVP-AUY922, PU-H17 and XL-888)

k) Selective COX-2 inhibitors (for example celecoxib), or non-selective NSAIDs (for example diclofenac, flurbiprofen, ibuprofen, ketoprofen, or naproxen).

In another aspect, a compound of general formula (I) can be used in combination with radiation therapy. In yet another aspect, a compound of general formula (I) may be administered in combination with standard chemotherapy combinations such as, but not restricted to, CMF (cyclophosphamide, methotrexate and 5-fluorouracil), CAF (cyclophosphamide, doxorubicin and 5-fluorouracil), AC (doxorubicin and cyclophosphamide), FEC (5-fluorouracil, epirubicin, and cyclophosphamide), ACT or ATC (doxorubicin, cyclophosphamide, and paclitaxel), or CMFP (cyclophosphamide, methotrexate, 5-fluorouracil and prednisone).

The disclosure also provides pharmaceutical compositions comprising one or more compounds of this disclosure and one or more pharmaceutically acceptable excipient and/or diluent. The pharmaceutical compositions can be chosen on the basis of the treatment requirements. Such compositions are prepared by blending and are suitably adapted to oral or parenteral administration, and as such can be administered in the form of tablets, capsules, oral preparations, powders, granules, pills, injectable, or infusible liquid solutions, suspensions, or suppositories. A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In one embodiment, the subject is human.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Tablets and capsules for oral administration are normally presented in unit dose form and contain conventional excipients such as binders, fillers (including cellulose, mannitol, lactose), diluents, tableting agents, lubricants (including magnesium stearate), detergents, disintegrants (e.g. polyvinylpyrrolidone and starch compounds such as sodium glycolate starch), coloring agents, flavoring agents, and wetting agents (for example sodium lauryl sulfate).

The oral solid compositions can be prepared by conventional methods of blending, filling or tableting. The blending operation can be repeated to distribute the active principle throughout compositions containing large quantities of fillers. Such operations are conventional.

Oral liquid preparations can be in the form of, for example, aqueous or oily suspensions, solutions, emulsions, syrups or elixirs, or can be presented as a dry product for reconstitution with water or with a suitable vehicle before use. Such liquid preparations can contain conventional additives such as suspending agents, for example sorbitol, syrup, methyl cellulose, gelatin, hydroxyethyl cellulose, carboxymethyl cellulose, aluminium stearate gel, or hydrogenated edible fats; emulsifying agents, such as lecithin, sorbitan monooleate, or acacia; non-aqueous vehicles (which can include edible oils), such as almond oil, fractionated coconut oil, oily esters such as esters of glycerine, propylene glycol, or ethyl alcohol; preservatives, such as methyl or propyl p-hydroxybenzoate or sorbic acid, and if desired, conventional flavoring or coloring agents. Oral formulations also include conventional slow-release formulations such as enterically coated tablets or granules.

Pharmaceutical preparation for administration by inhalation can be delivered from an insufflator or a nebulizer pressurized pack.

For parenteral administration fluid unit dosages can be prepared, containing the compound and a sterile vehicle. The compound can be either suspended or dissolved, depending on the vehicle and concentration. The parenteral solutions are normally prepared by dissolving the compound in a vehicle, sterilising by filtration, filling suitable vials and sealing. Advantageously, adjuvants such as local anaesthetics, preservatives and buffering agents can also be dissolved in the vehicle. To increase the stability, the composition can be frozen after having filled the vials and removed the water under vacuum. Parenteral suspensions are prepared in substantially the same manner, except that the compound can be suspended in the vehicle instead of being dissolved, and sterilized by exposure to ethylene oxide before suspending in the sterile vehicle. Advantageously, a surfactant or wetting agent can be included in the composition to facilitate uniform distribution of the compound of the disclosure.

For buccal or sublingual administration the compositions may be tablets, lozenges, pastilles, or gel.

The compounds can be pharmaceutically formulated as suppositories or retention enemas, e.g. containing conventional suppositories bases such as cocoa butter, polyethylene glycol, or other glycerides, for a rectal administration.

Another means of administering the compounds of the disclosure regards topical treatment. Topical formulations can contain for example ointments, creams, lotions, gels, solutions, pastes and/or can contain liposomes, micelles and/or microspheres. Examples of ointments include oleaginous ointments such as vegetable oils, animal fats, semisolid hydrocarbons, emulsifiable ointments such as hydroxystearin sulfate, anhydrous lanolin, hydrophilic petrolatum, cetyl alcohol, glycerol monostearate, stearic acid, water soluble ointments containing polyethylene glycols of various molecular weights. Creams, as known to formulation experts, are viscous liquids or semisolid emulsions, and contain an oil phase, an emulsifier and an aqueous phase. The oil phase generally contains petrolatum and an alcohol such as cetyl or stearic alcohol. Formulations suitable for topical administration to the eye also include eye drops, wherein the active ingredient is dissolved or suspended in a suitable carrier, especially an aqueous solvent for the active ingredient.

A further method of administering the compounds of the disclosure regards transdermal delivery. Typical transdermal formulations comprise conventional aqueous and non-aqueous vectors, such as creams, oils, lotions or pastes or can be in the form of membranes or medicated patches.

A reference for the formulations is the book by Remington ("Remington: The Science and Practice of Pharmacy", Lippincott Williams & Wilkins, 2000).

The compounds of the present disclosure may be employed alone as a sole therapy or in combination with one or more other therapeutic agents (see the list of additional agents is as indicated previously and comprises also standard chemotherapeutic agents) for the treatment of the above-mentioned conditions. The combination can be administered as separate compositions (simultaneous, sequential) of the individual components of the treatment or as a single dosage form containing one or more agents. When the compounds of this disclosure are in combination with one or more other active ingredients, the active ingredients may be separately formulated into single-ingredient preparations of one of the above-described forms and then provided as combined preparations, which are given at the same time or different times, or may be formulated together into a two—or more—ingredient preparation.

Compounds of general formula (I) may be administered to a patient in a total daily dose of, for example, from 0.001 to 1000 mg/kg body weight daily. Dosage unit compositions may contain such amounts of submultiples thereof to make up the daily dose. The determination of optimum dosages for a particular patient is well known to one skilled in the art.

As is common practice, the compositions are normally accompanied by written or printed instructions for use in the treatment in question.

The following non-limiting examples and biological data are presented and reference to the following the Figures is made in order to further illustrate the disclosure.

EXAMPLES

1. Chemical Synthesis

Unless otherwise indicated, commercially available reagents and solvents (HPLC grade) were used without further purification. Specifically, the following abbreviations may have been used in the descriptions of the experimental methods:

| | |
|---|---|
| NMR (Nuclear Magnetic Resonance) | $^1$H (proton) |
| MHz (Megahertz) | Hz (Hertz) |
| HPLC (High Performance Liquid Chromatography) | LC-MS (Liquid Chromatography Mass Spectrum) |
| s (seconds) | min (minutes) |
| h (hours) | mg (milligrams) |
| g (grams) | μL (microliters) |
| mL (millilitres) | mmol (millimoles) |
| nm (nanometers) | μM (micromolar) |
| M (molarity) | $R_t$ (retention time in minutes) |
| RT (room temperature) | MW (microwave) |
| AcOH (acetic acid) | BOC or boc (tert-butyloxycarbonyl) |
| $CH_2Cl_2$ (dichloromethane) | $CH_3CN$ (acetonitrile) |
| DME (1,2-dimethoxyethane) | DMF (dimethylformamide) |
| DMSO (dimethyl sulfoxide) | DMSO-$d_6$ (deuterated dimethyl |

39
-continued

| | sulfoxide) |
|---|---|
| Et₂O (diethyl ether) | EtOAc (ethyl acetate) |
| EtOH (ethanol) | HCl (hydrochloric acid) |
| K₂CO₃ (potassium carbonate) | MeOH (methanol) |
| Na₂CO₃ (sodium carbonate) | Na₂SO₄ (sodium sulphate) |
| NH₃ (ammonia) | NH₄Cl (ammonium chloride) |
| TEA (triethylamine) | tert-BuOH (tert-butanol) |

Except where indicated otherwise, all temperatures are expressed in ° C. (degrees centigrade) or K (Kelvin).

The ¹H-NMR spectra were acquired with a Varian 500 MHz instrument or, if stated explicitly, at 400 MHz on a Bruker AC 400 spectrometer. The chemical shifts are expressed in parts per million (ppm, δ units). The coupling constants are expressed in Hertz (Hz) and the splitting patterns are described as s (singlet), bs (broad signal), d (doublet), t (triplet), q (quartet), quint (quintet), m (multiplet).

The LC-MS analyses were carried out on a Waters Acquity UPLC or Waters Acquity UPLC H-Class linked to with a SQD Single quadrupole (Waters) using an Acquity UPLC BEH C18 (50×2.1 mm, 1.7 μm) or Acquity UPLC HSS T3 (50×2.1 mm, 1.8 μm) column. Phase A was composed by either Milli-Q water/CH₃CN 95/5+0.07% formic acid or Milli-Q water+0.07% formic acid; Phase B by CH₃CN+0.05% formic acid; flow rate: 0.6 mL/min; UV detection (DIODE array) from 210 to 400 nm; ESI+ detection in the 100-2000 m/z range. The yields were calculated assuming that products were 100% pure if not stated otherwise.

Intermediate 1: 3-(2-Oxooxazolidin-3-yl)benzamide

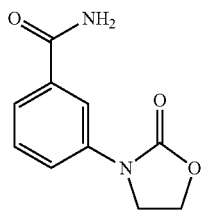 [SMILES: NC(=O)c1cccc(N2CCOC2=O)c1]

A suspension of 0.56 g (2.7 mmol) 3-(2-oxooxazolidin-3-yl)benzoic acid (WO2003/045913) in 15 mL dry CH₂Cl₂ was treated with 0.246 mL (3.38 mmol) thionyl chloride and 2 drops of dry DMF. After stirring at reflux for 2 h, the mixture was cooled to RT and poured in 4 mL NH₃ (28-30% in water). After 1 h the resulting mixture was filtered off to afford a white solid that was washed with water. The aqueous phases were extracted with CH₂Cl₂, and the combined organic layers were dried over Na₂SO₄ and filtered to give 0.549 g of 3-(2-oxooxazolidin-3-yl)benzamide (98%) as a white solid. ¹H NMR (DMSO-d₆) δ (ppm): 8.01 (bs, 1H), 7.94-7.88 (m, 1H), 7.84-7.78 (m, 1H), 7.61 (d, J=7.8 Hz, 1H), 7.52-7.34 (m, 2H), 4.49-4.39 (m, 2H), 4.14-3.98 (m, 2H); MS (ESI): m/z: 207 [M+H]+.

40
Intermediate 2: 4-(2-Oxo-1,3-oxazolidin-3-yl)benzamide

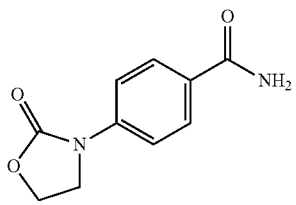 [SMILES: NC(=O)c1ccc(N2CCOC2=O)cc1]

Intermediate 2 was prepared according to the procedure for Intermediate 1 starting from 4-(2-oxo-1,3-oxazolidin-3-yl)benzoic acid (Enamine, Cat No. EN300-39599). ¹H NMR (DMSO-d₆) δ (ppm): 8.01-7.79 (m, 3H), 7.67-7.53 (m, 2H), 7.28 (bs, 1H), 4.44 (t, J=7.6 Hz, 2H), 4.08 (t, J=7.6 Hz, 2H); MS (ESI): m/z: 207 [M+H]+

Intermediate 3: (1R,2R)-2-(4-iodophenyl)cyclopropanecarboxylic acid

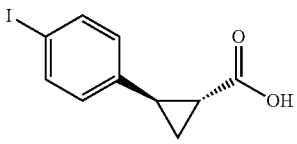 [SMILES: O=C(O)[C@@H]1C[C@H]1c1ccc(I)cc1]

Ethyl (1R,2R)-2-phenylcyclopropanecarboxylate 69 mL (173 mmol) of a 2.5 M solution of n-butyllithium in hexane was added at 25° C. dropwise over 5 min to a solution of 39 g (170 mmol) triethyl 2-phosphonoacetate in 75 mL of dry DME. The reaction mixture was stirred at RT for 5 min, then 16.0 g (133 mmol) of 5-styrene oxide (Sigma-Aldrich, cat. number 540102) was added in one portion. The reaction was heated at 135° C. for 60 min under MW. The orange reaction mixture was then cooled down to RT, saturated aqueous NH₄Cl was added and the product was extracted with Et₂O. The combined organic layers were dried over Na₂SO₄, filtered and the solvent was removed in vacuo. The crude product was filtered on a silica gel pad giving 21 g (83%) of ethyl (1R,2R)-2-phenylcyclopropanecarboxylate as yellow oil. ¹H NMR (CDCl₃) δ (ppm): 7.33-7.25 (m, 2H), 7.25-7.18 (m, 1H), 7.14-7.07 (m, 2H), 4.18 (q, J=7.3 Hz, 2H), 2.57-2.49 (m, 1H), 1.96-1.86 (m, 1H), 1.65-1.57 (m, 1H), 1.37-1.24 (m, 4H).

(1R,2R)-2-phenylcyclopropanecarboxylic acid 10.58 g (441.6 mmol) LiOH in 200 mL of H₂O was added to a solution of 21 g (110 mmol) of ethyl (1R,2R)-2-phenylcyclopropanecarboxylate dissolved in 220 mL of an ethanol/THF mixture (10;1, v:v) and the solution was heated at 115° C. for 50 min under MW irradiation. Then, the solution was concentrated, diluted with H₂O and quenched with 2 M HCl at 0° C. The precipitate was filtered off, washed with H₂O and triturated with Et₂O providing 14.85 g (83%) (1R,2R)-2-phenylcyclopropanecarboxylate as white solid. ¹H NMR (CDCl₃) δ (ppm): 9.91 (bs, 1H), 7.34-7.20 (m, 3H), 7.16-7.06 (m, 2H), 2.66-2.57 (m, 1H), 1.98-1.88 (m, 1H), 1.73-1.61 (m, 1H), 1.47-1.37 (m, 1H); MS (ESI): m/z: 161 [M−H]⁻

(1R,2R)-2-(4-iodophenyl)cyclopropanecarboxylic acid 13 g (50 mmol) of iodine, 4.5 g (21 mmol) potassium iodate and 7.5 mL concentrated $H_2SO_4$ in 75 ml of $H_2O$ was added to a stirred solution of 14.7 g (90.6 mmol) of (1R,2R)-2-phenylcyclopropanecarboxylic acid in 300 mL of AcOH. The mixture was heated to reflux for about 2 h, and then the reaction was stopped by adding 700 mL of 1 M $NaHSO_4$. The formed precipitate was filtered, dried and the resulting solid was triturated with hexane providing 19 g of (1R,2R)-2-(4-iodophenyl)cyclopropanecarboxylic acid (73%) as white solid. ¹H NMR (DMSO-$d_6$) δ (ppm): 12.66-10.65 (m, 1H), 7.72-7.54 (m, 2H), 6.96-6.79 (m, 2H), 2.63-2.46 (m, 1H), 1.97-1.80 (m, 1H), 1.74-1.61 (m, 1H), 1.47-1.30 (m, 1H); MS (ESI): m/z: 287 [M−H]⁻

Intermediate 4:
(1S,2S)-2-(4-iodophenyl)cyclopropanecarboxylic acid

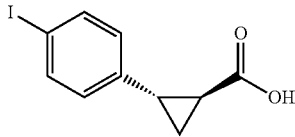 [SMILES: O=C(O)[C@H]1C[C@@H]1c1ccc(I)cc1]

(1S,2S)-2-(4-iodophenyl)cyclopropanecarboxylic acid was prepared according to the procedure described for (1R,2R)-2-(4-iodophenyl)cyclopropanecarboxylic acid (Intermediate 3) starting from (R)-styrene oxide (Sigma-Aldrich, cat. number 5400990). ¹H NMR (DMSO-$d_6$) δ (ppm): 12.29 (bs, 1H), 7.60 (d, J=8.3 Hz, 2H), 6.99 (d, J=8.3 Hz, 2H), 2.41-2.27 (m, 1H), 1.85-1.71 (m, 1H), 1.46-1.36 (m, 1H), 1.35-1.24 (m, 1H); MS (ESI): m/z: 287 [M−H]⁻

The synthesis of 4-(1-methylpiperidin-4-yl)benzamide is described in WO2009055077, of 4-(4-methylpiperazin-1-yl)benzamide in WO 2006/092510, and of 4-morpholinobenzamide in Eur. J. Med. Chem. 2010, 45, 3709-3718.

Example 1. N-[4-[trans-2-aminocyclopropyl]phenyl]-4-(4-methylpiperazin-1-yl)benzamide dihydrochloride

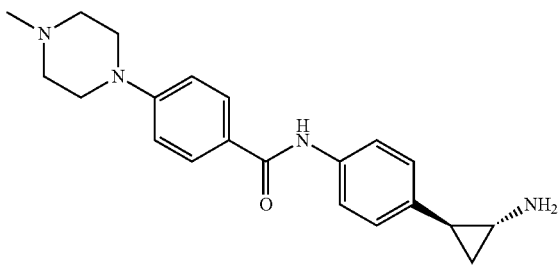

tert-butyl N-[trans-2-(4-iodophenyl)cyclopropyl] carbamate 7.4 g (27 mmol) Diphenyl phosphoryl azide and 4.4 mL (32 mmol) TEA were added to a solution of 7.05 g (24.5 mmol) of trans-2-(4-iodophenyl) cyclopropanecarboxylic acid (J. Med. Chem. 2012, 6624-6628) in 150 mL dry t-BuOH. After stirring at 90° C. for 20 h the solution was concentrated and the residue was partitioned between 10% aqueous $Na_2CO_3$ and $Et_2O$. The combined organic layers were dried over $Na_2SO_4$, filtered, and concentrated. The crude product was purified by flash chromatography (hexane/EtOAc 9:1, v:v) giving 5.2 g (57%) of tert-butyl N-[trans-2-(4-iodophenyl)cyclopropyl]carbamate as white solid. ¹H NMR (DMSO-$d_6$) δ (ppm): 7.67-7.51 (m, 2H), 7.25 (bs, 1H), 6.98-6.84 (m, 2H), 2.57 (bs, 1H), 1.89-1.74 (m, 1H), 1.37 (s, 9H), 1.18-0.95 (m, 2H); MS (ESI): m/z: 260 [MH−100]⁺

N-[trans-2-[4-[[4-(4-methylpiperazin-1-yl)benzoyl]amino]phenyl]cyclopropyl]carbamate 6 mg (0.03 mmol) CuI, 220 mg (0.613 mmol) tert-butyl N-[trans-2-(4-iodophenyl)cyclopropyl]carbamate, 0.15 mg (0.67 mmol) 4-(4-methylpiperazin-1-yl)benzamide and 0.17 g (1.23 mmol) $K_2CO_3$ were placed in a vial and charged with nitrogen. 5 mg (0.06 mmol) N,N'-dimethylethane-1,2-diamine and 2 mL dioxane were added with a syringe, and the vial was heated to 110° C. for 20 h. The resulting suspension was allowed to cool down to RT and was then filtered through a silica gel pad eluting with 25 ml of 9:1 $CH_2Cl_2$/MeOH. The filtrate was concentrated and the residue was purified by chromatography ($CH_2Cl_2$ to $CH_2Cl_2$/MeOH 95/5) to give 223 mg (81%) of N-[trans-2-[4-[[4-(4-methylpiperazin-1-yl)benzoyl]amino]phenyl]cyclopropyl]-carbamate as a white solid. ¹H NMR (DMSO-$d_6$) δ (ppm): 9.86 (s, 1H), 7.92-7.77 (m, 2H), 7.69-7.57 (m, 2H), 7.22 (bs, 1H), 7.08-6.90 (m, 4H), 3.31-3.15 (m, 4H), 2.62-2.53 (m, 1H), 2.47-2.36 (m, 4H), 2.22 (s, 3H), 1.90-1.79 (m, 1H), 1.38 (s, 9H), 1.13-1.02 (m, 2H); MS (ESI): m/z: 451 [M+H]⁺.

N-[4-[trans-2-aminocyclopropyl]phenyl]-4-(4-methylpiperazin-1-yl)benzamide dihydrochloride 2 mL of 2 M HCl in $Et_2O$ was added to a solution of 200 mg (0.44 mmol) of N-[trans-2-[4-[[4-(4-methylpiperazin-1-yl)benzoyl]amino]phenyl]cyclopropyl]carbamate in 3 mL $Et_2O$/MeOH (2:1, v:v) cooled down to 0° C. After stirring at RT for 20 h the formed precipitate was filtered off and the light yellow solid washed with $Et_2O$ and dried at 40° C. under vacuum giving 167 mg (89%) of N-[4-[trans-2-aminocyclopropyl]phenyl]-4-(4-methylpiperazin-1-yl)benzamide as its dihydrochloride salt. ¹H NMR (DMSO-$d_6$) δ (ppm): 9.97 (s, 1H), 9.75 (bs, 1H), 8.22 (bs, 3H), 7.98-7.83 (m, 2H), 7.77-7.63 (m, 2H), 7.20-6.98 (m, 4H), 4.14-3.93 (m, 2H), 3.60-3.45 (m, 2H), 3.18-2.98 (m, 4H), 2.87 (s, 3H), 2.83-2.74 (m, 1H), 2.27-2.17 (m, 1H), 1.35-1.27 (m, 1H), 1.24-1.14 (m, 1H); MS (ESI): m/z: 351 [M+H]⁺.

According to the procedure described for Example 1 Examples 2, 3, 4 and 5 were synthesized starting from the appropriate benzamide and tert-butyl N-[trans-2-(4-iodophenyl)cyclopropyl]carbamate.

Example 2. N-[4-[trans-2-aminocyclopropyl]phenyl]-4-(1-methyl-4-piperidyl)benzamide hydrochloride

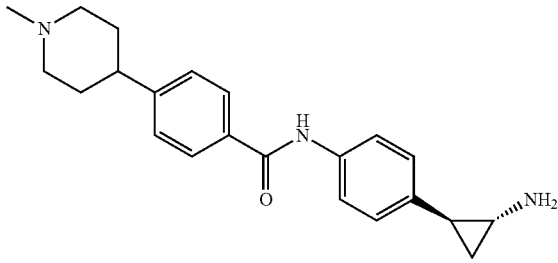 [SMILES: CN1CCC(c2ccc(C(=O)Nc3ccc([C@@H]4C[C@H]4N)cc3)cc2)CC1]

$^1$H NMR (DMSO-d$_6$) δ (ppm): 10.17 (s, 1H), 9.39 (bs, 1H), 8.23 (bs, 3H), 7.98-7.87 (m, 2H), 7.73-7.61 (m, 2H), 7.48-7.31 (m, 2H), 7.19-7.09 (m, 2H), 3.61-3.45 (m, 2H), 3.14-2.99 (m, 2H), 2.94-2.75 (m, 5H), 2.30-2.19 (m, 1H), 2.12-1.98 (m, 2H), 1.93-1.78 (m, 2H), 1.36-1.28 (m, 1H), 1.23-1.14 (m, 1H); MS (ESI): m/z: 350 [M+H]$^+$.

Example 3. N-[4-[trans-2-aminocyclopropyl]phenyl]-3-(2-oxooxazolidin-3-yl)benzamide hydrochloride

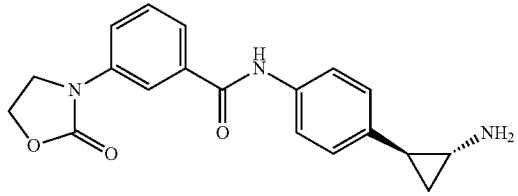 [SMILES: N[C@@H]1C[C@H]1c1ccc(NC(=O)c2cccc(N3CCOC3=O)c2)cc1]

$^1$H NMR (DMSO-d$_6$) δ (ppm): 10.29 (5, 1 H), 8.31 (bs, 3H), 8.07-8.00 (m, 1H), 7.84-7.77 (m, 1H), 7.73-7.66 (m, 3H), 7.59-7.50 (m, 1H), 7.19-7.12 (m, 2H), 4.51-4.43 (m, 2H), 4.20-4.08 (m, 2H), 2.87-2.75 (m, 1H), 2.32-2.21 (m, 1H), 1.39-1.29 (m, 1H), 1.27-1.15 (m, 1H); MS (ESI): m/z: 338 [M+H]$^+$.

Example 4. N-[4-[trans-2-aminocyclopropyl]phenyl]-4-morpholino-benzamide Hydrochloride

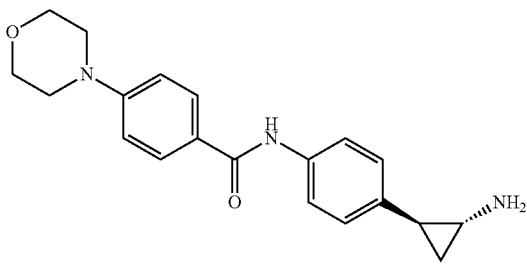 [SMILES: N[C@@H]1C[C@H]1c1ccc(NC(=O)c2ccc(N3CCOCC3)cc2)cc1]

$^1$H NMR (DMSO-d$_6$) δ (ppm): 9.93 (s, 1H), 8.31 (bs, 3H), 7.93-7.81 (m, 2H), 7.74-7.62 (m, 2H), 7.17-7.07 (m, 2H), 7.05-6.96 (m, 2H), 3.79-3.68 (m, 4H), 3.29-3.19 (m, 4H), 2.85-2.71 (m, 1H), 2.31-2.19 (m, 1H), 1.40-1.27 (m, 1H), 1.23-1.14 (m, 1H); MS (ESI): m/z: 338 [M+H]$^+$.

Example 5. N-[4-[trans-2-aminocyclopropyl]phenyl]-4-(2-oxooxazolidin-3-yl)benzamide Hydrochloride

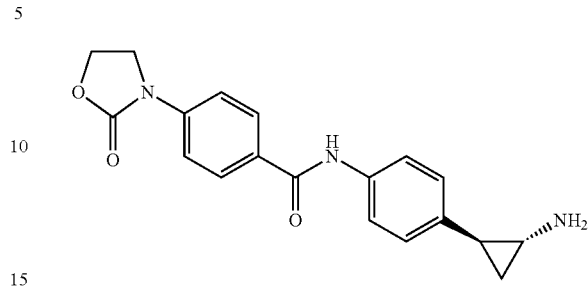

$^1$H NMR (DMSO-d$_6$) δ (ppm): 10.16 (s, 1H), 8.12 (bs, 3H), 8.02-7.96 (m, 2H), 7.74-7.66 (m, 4H), 7.18-7.08 (m, 2H), 4.55-4.40 (m, 2H), 4.20-4.02 (m, 2H), 2.85-2.74 (m, 1H), 2.31-2.15 (m, 1H), 1.36-1.13 (m, 2H); MS (ESI): m/z: 338 [M+H]$^+$.

Example 6. Benzyl N-[4-[[4-[trans-2-aminocyclopropyl]phenyl]carbamoyl]-2-(4-methylpiperazin-1-yl)phenyl]carbamate Dihydrochloride

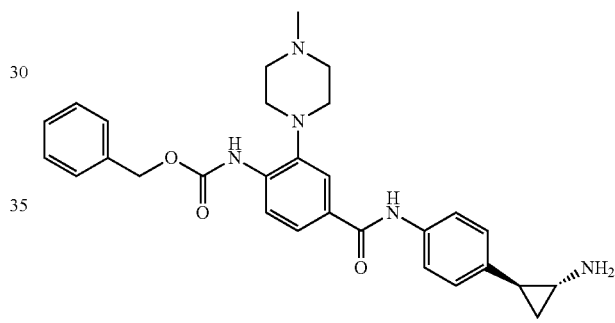

tert-Butyl 3-(4-methylpiperazin-1-yl)-4-nitrobenzoate

A suspension of tert butyl 3-chloro-4-nitro-benzoate (7.76 mmol, 2 g, (Bujok, R. et al. Tetrahedron 2010, 66, 698-708), dry K$_2$CO$_3$ (23.3 mmol, 3.22 g) and N-methylpiperazine (23.3 mmol, 2.58 mL) was stirred in dry DMF (10 mL) at 90° C. for 5 h in a sealed tube. After this time the reaction mixture was quenched with water (50 mL) and extracted with EtOAc, washed with brine and dried over Na$_2$SO$_4$. The collected organic phases were concentrated and the residue was purified on silica gel (eluent: EtOAc) to obtain tert-butyl 3-(4-methylpiperazin-1-yl)-4-nitrobenzoate as a yellow solid. $^1$H NMR (CDCl$_3$, 400 MHz) δ (ppm): 1.60 (s, 9H, —COOC(CH$_3$)$_3$), 2.37 (s, 3H, —NCH$_3$), 2.59 (t, 4H, CH$_3$N(CH$_2$)$_2$), 3.20 (t, 4H, -PhN(CH$_2$)$_2$), 7.07-7.09 (d, 1H, benzene proton), 8.03-8.05 (d, 1H, benzene proton), 8.37 (s, 1H, benzene proton); $^{13}$C NMR (CDCl$_3$, 100 MHz) δ (ppm): 28.8 (3C), 46.8, 51.5 (2C), 57.4 (2C), 81.3, 113.7, 120.6, 124.7, 137.3, 139.8, 143.5, 164.7; MS (EI) m/z: 321.17 [M]$^+$.

tert-Butyl 4-amino-3-(4-methylpiperazin-1-yl)benzoate

A suspension of tert-butyl 3-(4-methylpiperazin-1-yl)-4-nitrobenzoate (2.5 mmol, 0.8 g) in MeOH (30 mL) and 10% palladium on carbon (0.12 mmol, 0.13 g) was placed in a Parr apparatus and was hydrogenated at 50 psi and 25° C. for 5 h. The palladium was then filtered off and the MeOH was evaporated to afford an oily residue that was purified on silica gel (eluent: CHCl$_3$/MeOH, 10:1, v:v) to provide tert-butyl 4-amino-3-(4-methylpiperazin-1-yl)benzoate as a yellow solid. $^1$H NMR (CDCl$_3$, 400 MHz) δ (ppm): 1.58 (s, 9H, —COOC(CH$_3$)$_3$), 2.39 (s, 3H, —NCH$_3$), 2.60 (t, 4H, —N(CH$_2$)$_2$), 2.97 (t, 4H, -PhN(CH$_2$)$_2$), 4.35 (bs, 2H, -PhNH$_2$), 6.68-6.70 (d, 1H, benzene proton), 7.62-7.64 (d, 1H, benzene proton), 7.71 (s, 1H, benzene proton); $^{13}$C NMR (CDCl$_3$, 100 MHz) δ (ppm): 28.9 (3C), 46.7, 52.4 (2C), 57.2 (2C), 81.9, 113.3, 117.2, 120.5, 121.6, 137.7, 139.1, 164.8; MS (EI) m/z: 291.19 [M]$^+$.

tert-Butyl 4-(benzyloxycarbonylamino)-3-(4-methyl-piperazin-1-yl)benzoate

Benzyl chloroformate (2.1 mmol, 0.3 mL) was slowly added at 0° C. to a solution of tert-butyl 4-amino-3-(4-methylpiperazin-1-yl)benzoate (1.72 mmol; 0.5 g) in THF (10 mL) and TEA (2.1 mmol, 0.29 mL). The resulting mixture was stirred at RT for 1.5 h, then it was quenched with water (20 mL) and extracted with CH$_2$Cl$_2$ (3×20 mL). The organic phases were washed with brine, dried over Na$_2$SO$_4$ and concentrated to afford a residue that was purified on silica gel (eluent EtOAc/CHCl$_3$, 1:1, v:v) providing tert-butyl 4-(benzyloxycarbonylamino)-3-(4-methylpiperazin-1-yl)benzoate (72%). $^1$H NMR (CDCl$_3$, 400 MHz) δ (ppm): 1.60 (s, 9H, —COOC(CH$_3$)$_3$), 2.39 (s, 3H, —NCH$_3$), 2.62 (t, 4H, CH$_3$N(CH$_2$)$_2$), 2.92 (t, 4H, -PhN(CH$_2$)$_2$), 5.28 (s, 2H, —NHCOOCH$_2$Ph), 7.15-7.17 (d, 1H, benzene proton), 7.37-7.47 (m, 5H, —CH$_2$Ph), 7.69-7.72 (m, 2H, benzene protons), 8.69 (bs, 1H, —NHCOOCH$_2$Ph); $^{13}$C NMR (CDCl$_3$, 100 MHz) δ (ppm): 28.9 (3C), 46.3, 52.4 (2C), 57.5 (2C), 66.7, 81.4, 112.4, 119.9, 122.6, 125.3, 126.7, 127.3 (2C), 127.4, 129.1 (2C), 136.5, 142.7, 153.6, 164.7; MS (EI) m/z: 425.23 [M]+.

4-(benzyloxycarbonylamino)-3-(4-methylpiperazin-1-yl)benzoic acid

A solution of tert-butyl 4-(benzyloxycarbonylamino)-3-(4-methylpiperazin-1-yl)benzoate (0.47 mmol, 0.2 g) and TFA (9.4 mmol, 0.72 mL) in dry CH$_2$Cl$_2$ (5 mL) was stirred at RT overnight. The solvent was removed and the resulting solid was triturated with Et$_2$O (10 mL) to give 4-(benzyloxycarbonylamino)-3-(4-methylpiperazin-1-yl)benzoic acid as a colorless solid (83%). $^1$H NMR (DMSO-d$_6$, 400 MHz) δ (ppm): 2.87 (s, 3H, —NCH$_3$), 2.99-3.12 (m, 4H, CH$_3$N(CH$_2$)$_2$), 3.46-3.48 (t, 4H, -PhN(CH$_2$)$_2$), 5.23 (s, 2H, —NHCOOCH$_2$Ph), 7.36-7.47 (m, 5H, —CH$_2$Ph), 7.70 (s, 1H, benzene proton), 7.75-7.77 (d, 1H, benzene proton), 8.04-8.06 (d, 1H, benzene proton), 8.76 (bs, 1H, —NHCOOCH$_2$Ph), 9.72 (bs, 1H, NH$^+$), 12.88 (bs, 1H, —COOH); $^{13}$C NMR (DMSO-d$_6$, 400 MHz) δ (ppm): 46.7, 52.4 (2C), 57.2 (2C), 66.9, 112.5, 120.4, 122.7, 124.6, 126.2, 127.3 (2C), 127.5, 128.8 (2C), 136.3, 142.7, 154.1, 166.8; MS (EI) m/z: 369.17 [M]$^+$.

According to the procedure described for the preparation of 4-(benzyloxycarbonylamino)-3-(4-methylpiperazin-1-yl) benzoic acid the following intermediate compounds (Table 5) were synthesized starting from tert butyl 4-chloro-3-nitrobenzoate.

TABLE 5

| Molecular structure | Recrystallization Solvent, where necessary | m.p. (° C.) | Yield (%) |
|---|---|---|---|
| (piperidin-1-yl nitro tert-butyl benzoate) | toluene | 144-146 | 88 |
| (morpholin-4-yl nitro tert-butyl benzoate) | toluene | 149-151 | 85 |
| (4-methylpiperazin-1-yl nitro tert-butyl benzoate) | toluene | 138-140 | 92 |

TABLE 5-continued
| Molecular structure | Recrystallization Solvent, where necessary | m.p. (° C.) | Yield (%) |
|---|---|---|---|
| 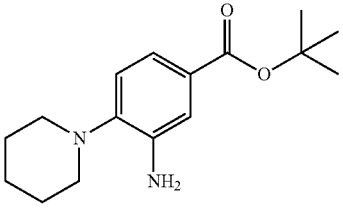 [SMILES: CC(C)(C)OC(=O)c1ccc(N2CCCCC2)c(N)c1] | cyclohexane | 115-117 | 67 |
| 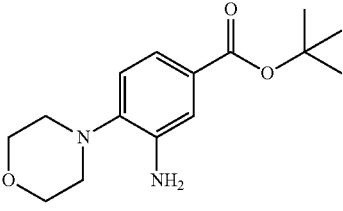 [SMILES: CC(C)(C)OC(=O)c1ccc(N2CCOCC2)c(N)c1] | cyclohexane | 126-128 | 73 |
| 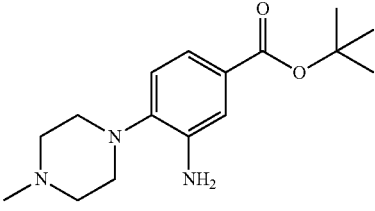 [SMILES: CN1CCN(c2ccc(C(=O)OC(C)(C)C)cc2N)CC1] | cyclohexane | 114-116 | 65 |
| 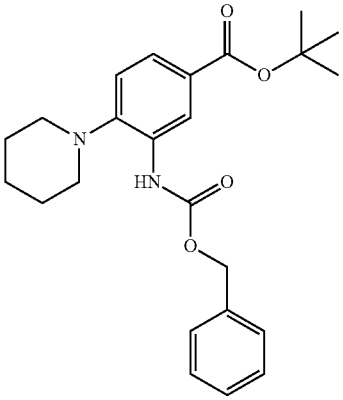 [SMILES: CC(C)(C)OC(=O)c1ccc(N2CCCCC2)c(NC(=O)OCc2ccccc2)c1] | — | oil | 68 |
| 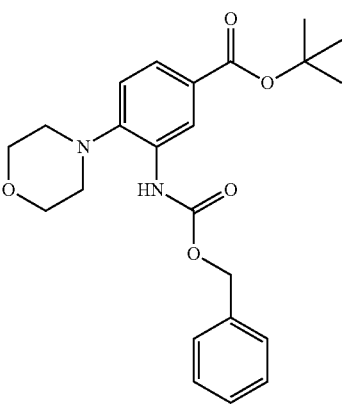 [SMILES: CC(C)(C)OC(=O)c1ccc(N2CCOCC2)c(NC(=O)OCc2ccccc2)c1] | — | oil | 71 |

TABLE 5-continued

| Molecular structure | Recrystallization Solvent, where necessary | m.p. (° C.) | Yield (%) |
|---|---|---|---|
| (structure) | — | oil | 65 |
| (structure) | — | oil | 72 |
| (structure) | acetonitrile | 214-216 | 86 |
| (structure) | acetonitrile | 234-236 | 83 |

TABLE 5-continued

| Molecular structure | Recrystallization Solvent, where necessary | m.p. (° C.) | Yield (%) |
|---|---|---|---|
| 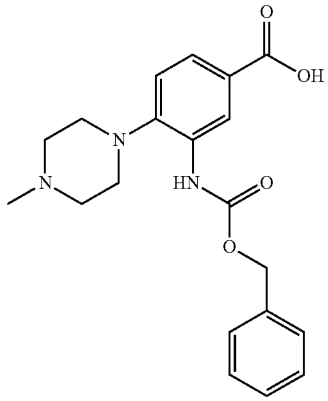 [SMILES: CN1CCN(c2ccc(C(=O)O)cc2NC(=O)OCc2ccccc2)CC1] | acetonitrile | 205-207 | 76 |

Benzyl N-[4-[[4-[trans-2-(tert-butoxycarbonylamino)cyclopropyl]phenyl]carbamoyl]-2-(4-methylpiperazin-1-yl)phenyl]carbamate TEA (1.08 mmol, 0.15 mL) and PyBop (0.32 mmol, 0.169 g) were added to a solution of 4-(benzyloxycarbonylamino)-3-(4-methylpiperazin-1-yl)benzoic acid (0.27 mmol, 0.1 g) in dry DMF under nitrogen atmosphere, and the resulting mixture was stirred at RT for 45 min. tert-Butyl N-[trans-2-(4-aminophenyl)cyclopropyl]carbamate (2.71 mmol, 0.067 g) was added under N$_2$ atmosphere and the reaction was continued overnight, then quenched with water (20 mL) and the product was extracted with CH$_2$Cl$_2$ (3×20 mL). The organic phases were washed with brine, dried over Na$_2$SO$_4$ and concentrated to furnish a residue that was purified by chromatography on silica gel (eluent: EtOAc/CHCl$_3$, 1:1, v:v) giving benzyl N-[4-[[4-[trans-2-(tert-butoxycarbonylamino)cyclopropyl]phenyl]carbamoyl]-2-(4-methylpiperazin-1-yl)phenyl]carbamate (74%). $^1$H NMR (CDCl$_3$, 400 MHz) δ (ppm): 1.18 (m, 1H, CHH cyclopropane), 1.37 (m, 1H, CHH cyclopropane), 1.5 (s, 9H, —C(CH$_3$)$_3$), 2.31 (m, 1H, CHNH$_2$), 2.80 (m, 4H, CH$_3$N(CH$_2$)$_2$), 3.15 (m, 4H, -PhN(CH$_2$)$_2$), 3.32-3.38 (m, 4H, —NCH$_3$ and PhCH), 4.89 (bs, 1H, NHCOOC(CH$_3$)$_3$), 5.23 (s, 2H, —NHCOOCH$_2$Ph), 7.13-7.16 (d, 2H, benzene protons), 7.34-7.48 (m, 5H, benzene protons), 7.70-7.72 (d, 2H, benzene protons), 7.79-7.86 (m, 2H, benzene protons), 8.01-8.03 (d, 1H, benzene proton), 8.74 (bs, 1H, —NHCOOCH$_2$Ph), 10.27 (bs, 1H, PhCONH), 11.12 (bs, 1H, NH$^+$); $^{13}$C NMR (CDCl$_3$, 100 MHz) δ (ppm): 14.5, 23.1, 28.6 (3C), 32.7, 46.8, 52.3 (2C), 57.4 (2C), 66.5, 79.8, 110.3, 119.5, 121.6 (2C), 122.6, 124.5, 125.3 (2C), 127.6 (2C), 127.9, 129.3 (2C), 130.8, 134.5, 136.4, 137.5, 143.3, 153.7, 155.8, 164.9; MS (EI) m/z: 599.31 [M]$^+$.

According to the procedure described for the preparation benzyl N-[4-[[4-[trans-2-(tert-butoxycarbonylamino)cyclopropyl]phenyl]carbamoyl]-2-(4-methylpiperazin-1-yl)phenyl]carbamate the following intermediate compounds were synthesized starting from the corresponding carboxylic acid and tert-butyl N-[trans-2-(4-aminophenyl)cyclopropyl]carbamate (Table 6).

TABLE 6

| Molecular structure | Recrystallization solvent | m.p. (° C.) | Yield (%) |
|---|---|---|---|
| 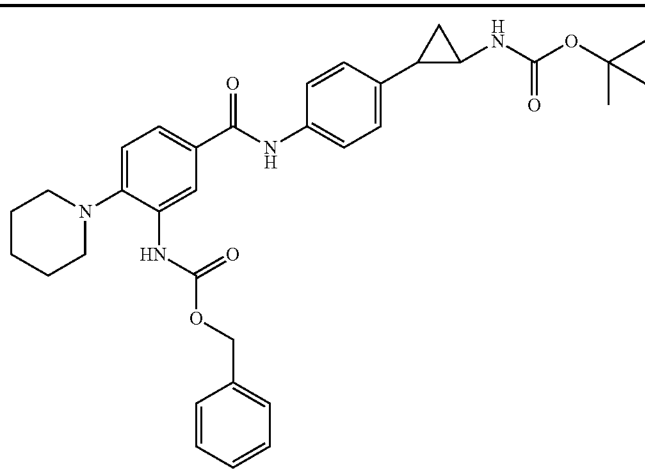 | cyclohexane | 116-118 | 72 |

TABLE 6-continued

| Molecular structure | Recrystallization solvent | m.p. (° C.) | Yield (%) |
|---|---|---|---|
| | cyclohexane | 118-120 | 75 |
| | cyclohexane | 125-127 | 68 |

Benzyl N-[4-[[4-[trans-2-aminocyclopropyl]phenyl]carbamoyl]-2-(4-methylpiperazin-1-yl)phenyl]carbamate dihydrochloride A solution of benzyl N-[4-[[4-[trans-2-(tert-butoxycarbonylamino)cyclopropyl]-phenyl]carbamoyl]-2-(4-methylpiperazin-1-yl)phenyl]carbamate (0.1 mmol, 0.06 g) and 4 M HCl (2.0 mmol, 0.5 mL) was stirred at RT overnight. The solid was then filtered off and washed with Et$_2$O (3×5 mL) to afford benzyl N-[4-[[4-[trans-2-aminocyclopropyl]phenyl]carbamoyl]-2-(4-methylpiperazin-1-yl)phenyl]carbamate dihydrochloride as a colorless solid (79%). $^1$H NMR (DMSO-ds, 400 MHz) δ (ppm): 1.20 (m, 1H, CHH cyclopropane), 1.39 (m, 1H, CHH cyclopropane), 2.34 (m, 1H, CHNH$_2$), 2.80 (m, 4H, CH$_3$N(CH$_2$)$_2$), 3.15 (m, 4H, -PhN(CH$_2$)$_2$), 3.32-3.38 (m, 4H, —NCH$_3$ and PhCH), 5.23 (s, 2H, —NHCOOCH$_2$Ph), 7.13-7.16 (d, 2H, benzene protons), 7.34-7.48 (m, 5H, benzene protons), 7.70-7.72 (d, 2H, benzene protons), 7.79-7.86 (m, 2H, benzene protons), 8.01-8.03 (d, 1H, benzene proton), 8.56 (bs, 3H, NH$_3^+$), 8.74 (bs, 1H, —NHCOOCH$_2$Ph), 10.27 (bs, 1H, PhCONH), 11.12 (bs, 1H, NH$^+$) ppm; $^{13}$C NMR (DMSO-d$_6$, 400 MHz) δ (ppm): 12.3, 20.6, 40.5, 46.8, 52.3 (2C), 57.3 (2C), 66.5, 110.3, 119.7, 121.1 (2C), 122.9, 124.3, 125.5 (2C), 127.2 (2C), 127.5, 129.3 (2C), 130.8, 134.7, 136.3, 137.2, 143.2, 153.8, 164.9 ppm; MS (EI) m/z: 499.26 [M]$^+$.

According to the procedure described for Example 6 the compounds of Examples 7, 8 and 9 were synthesized starting from the appropriate tert-butyl N-[trans-2-(4-aminophenyl)cyclopropyl]carbamate.

Example 7. Benzyl N-[5-[[4-[(trans-2-aminocyclopropyl]phenyl]carbamoyl]-2-(4-methylpiperazin-1-yl)phenyl]carbamate Dihydrochloride

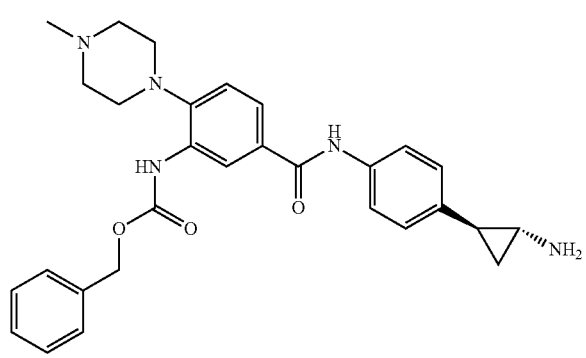 [SMILES: CN1CCN(c2ccc(C(=O)Nc3ccc([C@@H]4C[C@H]4N)cc3)cc2NC(=O)OCc2ccccc2)CC1]

¹H NMR (DMSO-d₆, 400 MHz) δ (ppm): 1.20 (m, 1H, CHH cyclopropane), 1.39 (m, 1H, CHH cyclopropane), 2.34 (m, 1H, CHNH₂), 2.83 (t, 4H, CH₃N(CH₂)₂), 3.15 (m, 4H, PhN(CH₂)₂), 3.33 (s, 3H, —NCH₃), 5.23 (s, 2H, —NHCOOCH₂Ph), 7.15-7.18 (d, 2H, benzene protons), 7.30-7.48 (m, 5H, benzene protons), 7.70-7.72 (d, 2H, benzene protons), 7.79-7.86 (m, 2H, benzene protons), 8.01-8.03 (d, 1H, benzene proton), 8.56 (bs, 3H, NH₃+), 8.74 (bs, 1H, —NHCOOCH₂Ph), 10.27 (bs, 1H, PhCONH), 11.12 (bs, 1H, NW); ¹³C NMR (DMSO-d₆, 100 MHz) δ (ppm): 17.3, 25.6, 34.4, 46.7, 52.1 (2C), 57.3 (2C), 66.8, 114.7, 118.2, 121.0, 121.3 (2C), 123.9, 125.5 (2C), 125.9, 127.4 (2C), 127.9, 129.0 (2C), 134.5, 136.3, 137.3, 146.4, 153.8, 164.8. MS (ESI) m/z: 500 ([M+H]⁺).

Example 8. Benzyl N-[5-[[4-[trans-2-aminocyclopropyl]phenyl]carbamoyl]-2-(1-piperidyl)phenyl] carbamate Hydrochloride

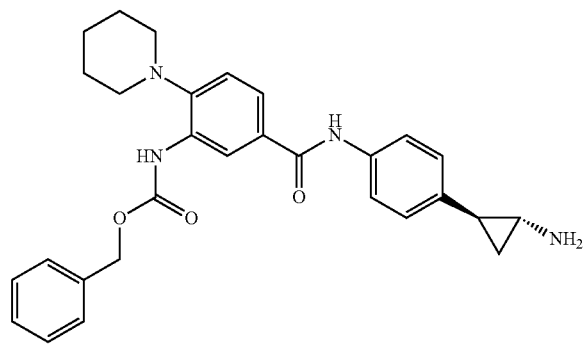 [SMILES: N[C@@H]1C[C@H]1c1ccc(NC(=O)c2ccc(N3CCCCC3)c(NC(=O)OCc3ccccc3)c2)cc1]

¹H NMR (DMSO-d₆, 400 MHz) δ (ppm): 1.20 (m, 1H, CHH cyclopropane), 1.39 (m, 1H, CHH cyclopropane), 1.52-1.59 (m, 6H, piperidine protons), 2.34 (m, 1H, CHNH₂), 3.0 (t, 4H, —N(CH₂)₂), 3.32-3.36 (m, 1H, PhCH), 5.23 (s, 2H, —NHCOOCH₂Ph), 7.14-7.17 (d, 2H, benzene protons), 7.32-7.46 (m, 5H, benzene protons), 7.68-7.70 (d, 2H, benzene protons), 7.79-7.86 (m, 2H, benzene protons), 8.02-8.04 (d, 1H, benzene proton), 8.56 (bs, 3H, NH₃⁺), 8.74 (bs, 1H, —NHCOOCH₂Ph), 10.30 (bs, 1H, PhCONH), 11.12 (bs, 1H, NW); ¹³C NMR (DMSO-d₆, 100 MHz) δ (ppm): 17.2, 24.5, 25.5 (2C), 25.7, 34.4, 54.7 (2C), 66.8, 114.8, 118.5, 120.8, 121.3 (2C), 124.0, 125.4 (2C), 125.9, 127.5 (2C), 127.7, 128.9 (2C), 134.5, 136.2, 137.3, 146.5, 153.9, 164.8. MS (ESI) m/z: 485 ([M+H]⁺).

Example 9. Benzyl N-[5-[[4-[trans-2-aminocyclopropyl]phenyl]carbamoyl]-2-morpholino-phenyl] carbamate hydrochloride

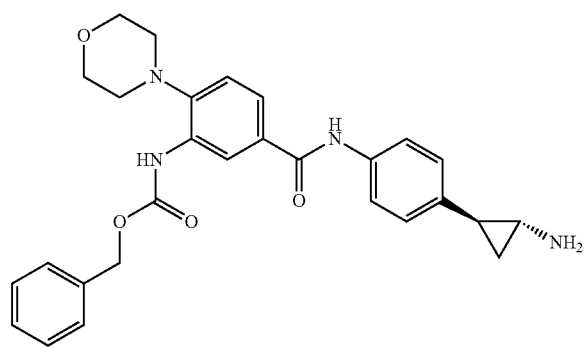

¹H NMR (DMSO-d₆, 400 MHz) δ (ppm): 1.21 (m, 1H, CHH cyclopropane), 1.38 (m, 1H, CHH cyclopropane), 2.33 (m, 1H, CHNH₂), 2.89 (t, 4H, —N(CH₂)₂), 3.88 (m, 4H, O(CH₂)₂), 5.27 (s, 2H, —NHCOOCH₂Ph), 7.15-7.18 (d, 2H, benzene protons), 7.32-7.46 (m, 5H, benzene protons), 7.71-7.73 (d, 2H, benzene protons), 7.79-7.86 (m, 2H, benzene protons), 8.03-8.05 (d, 1H, benzene proton), 8.58 (bs, 3H, NH₃⁺), 8.75 (bs, 1H, —NHCOOCH₂Ph), 10.30 (bs, 1H, PhCONH), 11.13 (bs, 1H, NH⁺). MS (ESI) m/z: 487 ([M+H]⁺).

Examples 10 and 11 were synthesized starting from (1R,2R)-2-(4-iodophenyl)cyclopropanecarboxylic acid (Intermediate 3) and Examples 12 and 13 starting from (1S,2S)-2-(4-iodophenyl)cyclopropanecarboxylic acid (Intermediate 4) according to the procedure described for Example 1.

Example 10. N-[4-[(1S,2R)-2-aminocyclopropyl]phenyl]-4-(4-methylpiperazin-1-yl)benzamide Dihydrochloride

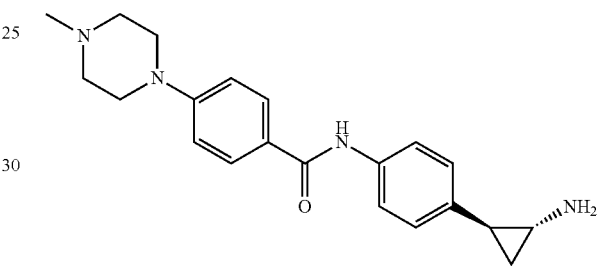

¹H NMR (DMSO-d₆) δ (ppm): 10.85 (bs, 1H), 10.00 (s, 1H), 8.44 (bs, 3H), 7.95-7.85 (m, 2H), 7.74-7.65 (m, 2H), 7.10 (dd, J=9.0, 12.5 Hz, 4H), 4.07-3.96 (m, 2H), 3.54-3.43 (m, 2H), 3.25-3.07 (m, 4H), 2.86-2.70 (m, 4H), 2.33-2.23 (m, 1H), 1.41-1.30 (m, 1H), 1.22-1.11 (m, 1H); MS (ESI): m/z: 351 [M+H]⁺; [α]_D −46.48 (c=0.00236 g/ml. DMSO).

Example 11. N-[4-[(1S,2R)-2-aminocyclopropyl]phenyl]-3-(2-oxoooxazolidin-3-yl)benzamide Hydrochloride

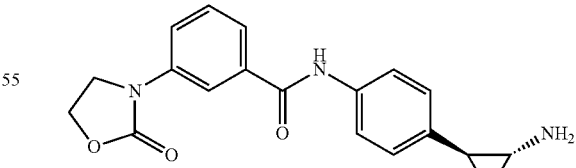

¹H NMR (DMSO-d₆) δ (ppm): 10.28 (s, 1H), 8.18 (s, 3H), 8.05-8.01 (m, 1H), 7.82-7.78 (m, 1H), 7.72-7.67 (m, 3H), 7.57-7.51 (m, 1H), 7.17-7.12 (m, 2H), 4.50-4.44 (m, 2H), 4.16-4.11 (m, 2H), 2.83-2.76 (m, 1H), 2.29-2.22 (m, 1H), 1.36-1.29 (m, 1H), 1.23-1.16 (m, 1H); MS (ESI): m/z: 338 [M+H]⁺; [α]_D −35.43 (c=0.00285 g/ml, DMSO).

Example 12. N-[4-[(1R,2S)-2-aminocyclopropyl]phenyl]-4-(4-methylpiperazin-1-yl)benzamide Dihydrochloride

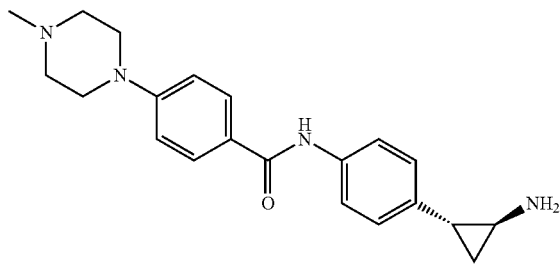 [SMILES: CN1CCN(c2ccc(C(=O)Nc3ccc([C@H]4C[C@@H]4N)cc3)cc2)CC1]

$^1$H NMR (DMSO-d$_6$) δ (ppm): 11.00 (bs, 1H), 10.01 (s, 1H), 8.48 (bs, 3H), 7.97-7.85 (m, 2H), 7.74-7.63 (m, 2H), 7.17-7.01 (m, 4H), 4.08-3.95 (m, 2H), 3.54-3.42 (m, 2H), 3.27-3.03 (m, 4H), 2.87-2.67 (m, 4H), 2.36-2.23 (m, 1H), 1.43-1.30 (m, 1H), 1.22-1.09 (m, 1H); MS (ESI): m/z: 351 [M+H]$^+$; [α]$_D$ +41.21 (c=0.00303 g/ml, DMSO).

Example 13. N-[4-[(1R,2S)-2-aminocyclopropyl]phenyl]-3-(2-oxooxazolidin-3-yl)benzamide Hydrochloride

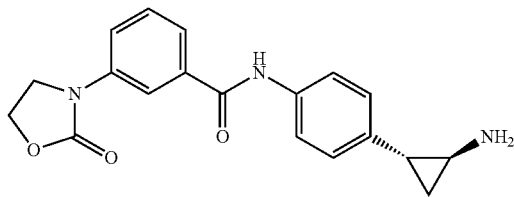

$^1$H NMR (DMSO-d$_6$) δ (ppm): 10.28 (s, 1H), 8.31 (s, 3H), 8.06-8.01 (m, 1H), 7.83-7.78 (m, 1H), 7.72-7.67 (m, 3H), 7.58-7.51 (m, 1H), 7.18-7.12 (m, 2H), 4.51-4.43 (m, 2H), 4.17-4.10 (m, 2H), 2.83-2.77 (m, 1H), 2.31-2.23 (m, 1H), 1.38-1.31 (m, 1H), 1.24-1.16 (m, 1H); MS (ESI): m/z: 338 [M+H]$^+$; [α]$_D$ +33.84 (c=0.00263 g/ml, DMSO).

2. Biological Testing

2.1 Assay of Enzyme Inhibition of KDM1A (LSD1)

The complex of human recombinant KDM1A (LSD1)/CoRest protein was produced in *E. coli* as separate proteins and co-purified following previously reported procedures (Forneris F. et al. Trends Biochem. Sci. 2008, 33, 181-189; Forneris F. et al. J. Biol. Chem. 2007, 282, 20070-20074). The experiments were performed using a mono-methylated H3-K4 peptide containing 21 amino acids (custom synthesis done by Thermo Scientific) as substrate and in 50 mM TRIS, pH 8.0 and 0.05 mg/ml BSA. The peptide purity was >90% as checked by analytical high-pressure liquid chromatography and mass spectrometry.

The demethylase activity was estimated under aerobic conditions and at RT by measuring the release of $H_2O_2$ produced during the catalytic process by the Amplex® UltraRed detection system coupled with peroxidase assay. Briefly, a fixed amount of KDM1A/CoRest complex was incubated at RT for 15 min in the absence and/or the presence of various concentrations of the inhibitors (e.g. from 0 to 100 μM, depending on the inhibitor strength) and of Amplex® UltraRed detection system coupled with peroxidase assay. The inhibitors were tested twice in duplicates at each concentration. Tranylcypromine (Sigma) was used as control. After preincubation of the enzyme with the inhibitor, 4.5 μM of mono-methylated H3-K4 peptide was added and the experiment was left for additional 12 min. The conversion of the Amplex® Ultra Red reagent to resorufin was monitored in continuous by fluorescence (excitation at 540 nm, emission at 590 nm) using a microplate reader (Infinite 200, Tecan). Arbitrary units were used to measure the level of $H_2O_2$ produced in the absence and/or in the presence of inhibition. The maximum demethylase activity of KDM1A/CoRest was obtained in the absence of inhibitors and corrected for background fluorescence in the absence of KDM1A/CoRest. The IC$_{50}$ was calculated using GraphPad Software.

Compounds 1-13 exhibited IC$_{50}$ values of less than 1.0 μM.

2.2 Cell Growth

CellTiter-Flor® (Promega) is a nonlytic, single-reagent-addition fluorescence assay that measures the relative number of living cells in a culture population after experimental manipulation. The CellTiter-Fluor™ Cell Viability Assay measures the conserved and constitutive protease activity within live cells and therefore acts as a marker for cell viability.

Human leukemia MV4-11 cells, (obtained from the Deutsche Sammlung von Mikroorganismen and Zellkulturen, ACC 102) in exponential growth, were incubated for 48 h with different concentrations of the inhibitors (e.g. from 0 to 100 μM). After 48 h a volume of CellTiterFluor® Reagent equal to the volume of cell culture medium was added. The content was mixed and incubates for at least 90 min at 37° C. degree to obtain a stable signal. The fluorescence was recorded using an excitation wavelength of 360 nm and an emission at 535 nm. The IC$_{50}$ was calculated using GraphPad Software.

The obtained results are illustrated in Table 7. IC$_{50}$ results were allocated to one of 3 ranges as follows: Range A: IC$_{50}$ from 50 to 100 μM; Range B: from 5 to 50 μM; Range C: IC$_{50}$ ≤5 μM.

TABLE 7

Results of the cell growth inhibitory assay:

| Cpd | Name | Structure | IC$_{50}$ [μM] |
|---|---|---|---|
| 5b* | N-[4-[trans-2-aminocyclopropyl]phenyl]benzamide | 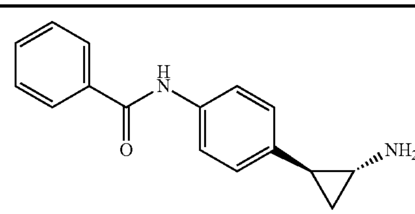 | A |

TABLE 7-continued

Results of the cell growth inhibitory assay:

| Cpd | Name | Structure | IC$_{50}$ [μM] |
|---|---|---|---|
| 5e* | N-[4-[trans-2-aminocyclopropyl]phenyl]-4-phenyl-benzamide | 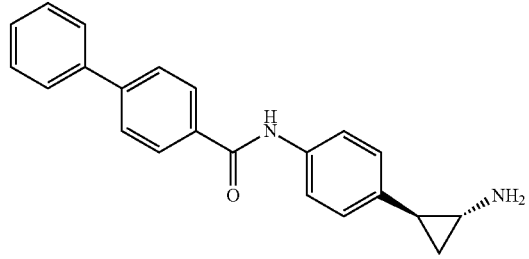 [SMILES: N[C@@H]1C[C@H]1c1ccc(NC(=O)c2ccc(-c3ccccc3)cc2)cc1] | C |
| 1 | N-[4-[trans-2-aminocyclopropyl]phenyl]-4-(4-methylpiperazin-1-yl)benzamide dihydrochloride | 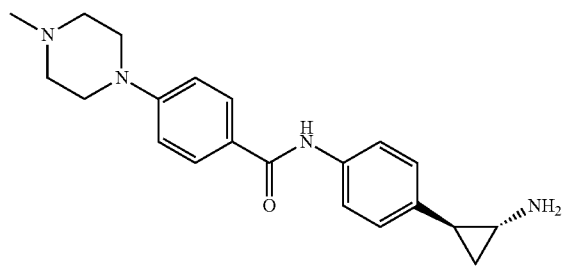 [SMILES: CN1CCN(c2ccc(C(=O)Nc3ccc([C@@H]4C[C@H]4N)cc3)cc2)CC1] | C |
| 2 | N-[4-[trans-2-aminocyclopropyl]phenyl]-4-(1-methyl-4-piperidyl)benzamide hydrochloride | 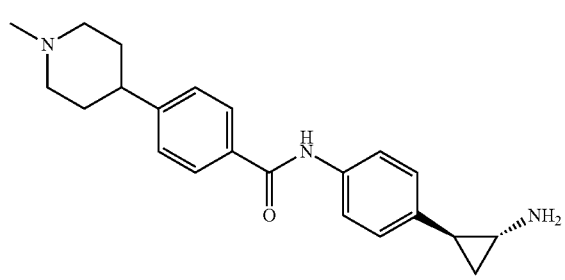 [SMILES: CN1CCC(c2ccc(C(=O)Nc3ccc([C@@H]4C[C@H]4N)cc3)cc2)CC1] | C |
| 3 | N-[4-[trans-2-aminocyclopropyl]phenyl]-3-(2-oxooxazolidin-3-yl)benzamide hydrochloride | 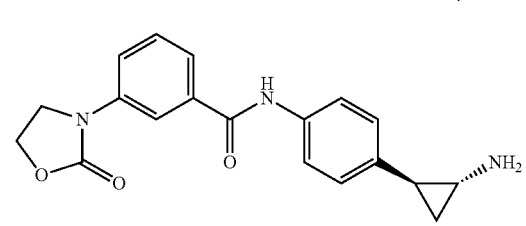 | C |
| 4 | N-[4-[trans-2-aminocyclopropyl]phenyl]-4-morpholino-benzamide hydrochloride | 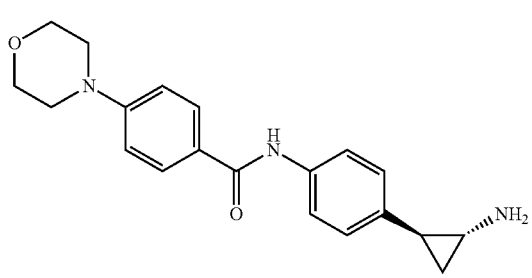 [SMILES: N[C@@H]1C[C@H]1c1ccc(NC(=O)c2ccc(N3CCOCC3)cc2)cc1] | B |
| 5 | N-[4-[trans-2-aminocyclopropyl]phenyl]-4-(2-oxooxazolidin-3-yl)benzamide hydrochloride | 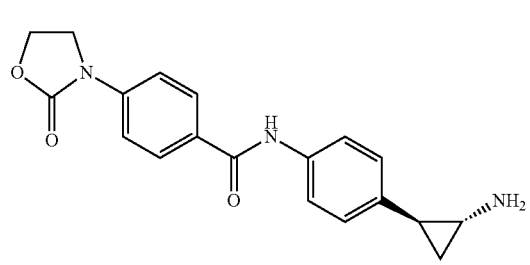 [SMILES: N[C@@H]1C[C@H]1c1ccc(NC(=O)c2ccc(N3CCOC3=O)cc2)cc1] | B |

TABLE 7-continued

Results of the cell growth inhibitory assay:

| Cpd | Name | Structure | IC$_{50}$ [μM] |
|---|---|---|---|
| 6 | benzyl N-[4-[[4-[trans-2-aminocyclopropyl]phenyl]carbamoyl]-2-(4-methylpiperazin-1-yl)phenyl]carbamate dihydrochloride | 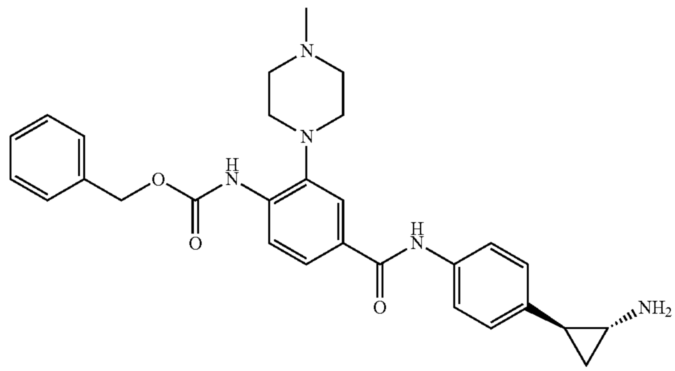 [SMILES: CN1CCN(c2cc(C(=O)Nc3ccc([C@@H]4C[C@H]4N)cc3)ccc2NC(=O)OCc2ccccc2)CC1] | C |
| 7 | benzyl N-[5-[[4-[(trans-2-aminocyclopropyl]phenyl]carbamoyl]-2-(4-methylpiperazin-1-yl)phenyl]carbamate dihydrochloride | 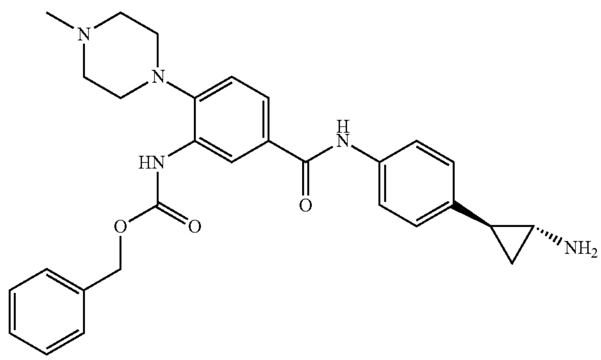 [SMILES: CN1CCN(c2ccc(C(=O)Nc3ccc([C@@H]4C[C@H]4N)cc3)cc2NC(=O)OCc2ccccc2)CC1] | C |
| 8 | benzyl N-[5-[[4-[trans-2-aminocyclopropyl]phenyl]carbamoyl]-2-(1-piperidyl)phenyl]carbamate hydrochloride | 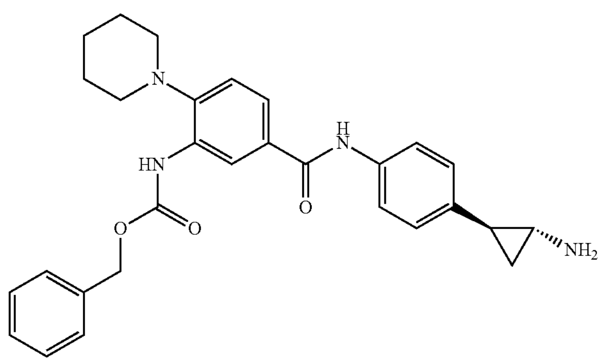 [SMILES: N[C@@H]1C[C@H]1c1ccc(NC(=O)c2ccc(N3CCCCC3)c(NC(=O)OCc3ccccc3)c2)cc1] | C |
| 9 | benzyl N-[5-[[4-[trans-2-aminocyclopropyl]phenyl]carbamoyl]-2-morpholino-phenyl]carbamate hydrochloride | 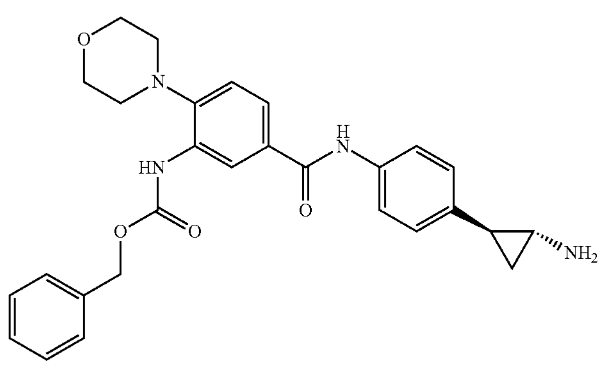 [SMILES: N[C@@H]1C[C@H]1c1ccc(NC(=O)c2ccc(N3CCOCC3)c(NC(=O)OCc3ccccc3)c2)cc1] | C |

TABLE 7-continued

Results of the cell growth inhibitory assay:

| Cpd | Name | Structure | IC$_{50}$ [μM] |
|-----|------|-----------|----------------|
| 10 | N-[4-[(1S,2R)-2-aminocyclopropyl]phenyl]-4-(4-methylpiperazin-1-yl)benzamide dihydrochloride | 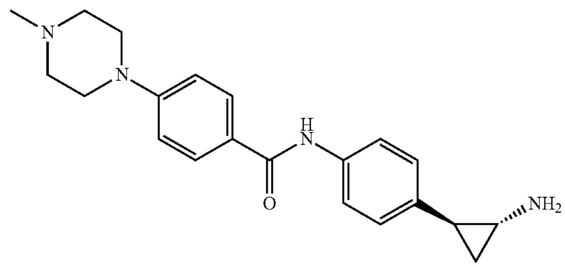 | C |
| 11 | N-[4-[(1S,2R)-2-aminocyclopropyl]phenyl]-3-(2-oxooxazolidin-3-yl)benzamide hydrochloride | 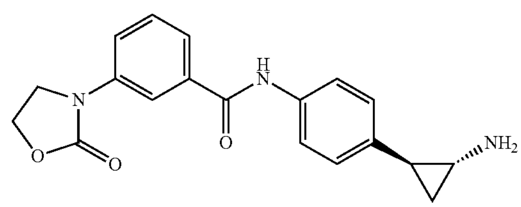 [SMILES: N[C@@H]1C[C@H]1c1ccc(NC(=O)c2cccc(N3CCOC3=O)c2)cc1] | C |
| 12 | N-[4-[(1R,2S)-2-aminocyclopropyl]phenyl]-4-(4-methylpiperazin-1-yl)benzamide dihydrochloride | 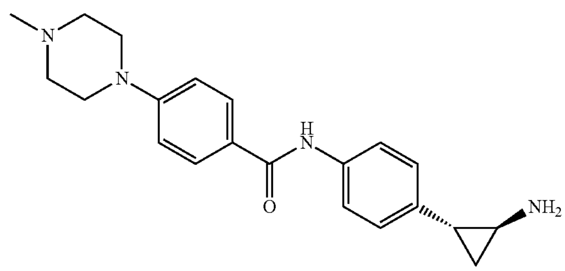 [SMILES: CN1CCN(c2ccc(C(=O)Nc3ccc([C@H]4C[C@@H]4N)cc3)cc2)CC1] | B |
| 13 | N-[4-[(1R,2S)-2-aminocyclopropyl]phenyl]-3-(2-oxooxazolidin-3-yl)benzamide hydrochloride | 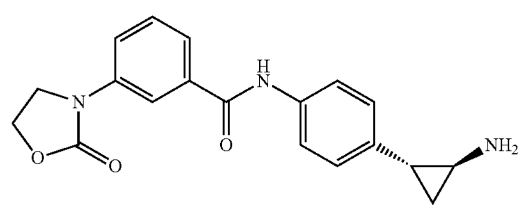 [SMILES: N[C@H]1C[C@@H]1c1ccc(NC(=O)c2cccc(N3CCOC3=O)c2)cc1] | C |

*compound 5b and 5e of WO2011/131576

2.3 Bioluminescent-Coupled Assay for Monoamine Oxidases (MAO-Glo Assay)

The MAO-Glo Assay from Promega (cat. V1402, Promega, Madison, Wis.) was used to measure the effect of inhibitors on MAO-A and MAO-B activity.

Human recombinant MAO A and MAO B were expressed in *Pichia pastoris* and purified as published (Binda C. et al. Proc. Natl. Acad. Sci. USA, 2003, 9750-9755). The assay was performed at RT in 50 μL (25 μL reaction solution+25 μL detection reagent) in 96 well half area white plates (cat. 3693, Corning, Corning, N.Y.). Luminescence was measured after 20 min incubation in the dark using a microplate reader (Infinite F200, Tecan Group, Switzerland) with an integration time of 0.25 s per well.

50 nM MAO-A or 125 nM MAO-B were incubated with five different inhibitor concentrations (from 0.004 μM to 100 μM) for 15 min at RT in Promega MAO Buffer or Promega MAO-B Buffer (MAO-Glo Assay kit, catalogue number V1402, Promega, Madison, Wis.). The Promega MAO substrate was at a concentration equal to the calculated K$_m$ (40 μM for MAO-A and 14 μM for MAO-B). After 30 min of incubation the reaction was stopped with the Promega detection reagent. The experiments were carried out in duplicate. IC$_{50}$ was calculated using GraphPad Prism version 4.0 (GraphPad Software, San Diego, Calif.). In order to determine if any of the compounds inhibit the Luciferin Detection Reagent, each compound was re-screened in the absence of MAOs using 0.5 μM D-luciferin methyl ester as substrate (Michael P. et al. Cell Notes, 2006, 14, 4-7, Promega Corporation and Promega Biosciences, Inc).

Table 8 reports the ratio of the IC$_{50}$ values against MAO-A over those obtained for LSD1 of compounds of this disclosure and the representative compound 5b of PCT application WO2011/131576 (the IC$_{50}$ values for compound 5b were established according to the above described protocol, in specific after a pre-incubation of 15 min of the compound with the enzyme before performing the assay).

TABLE 8

| Cpd | Name | Structure | IC$_{50}$ (MAO-A)/ IC$_{50}$ (LSD1) |
|---|---|---|---|
| 5b* | N-[4-[trans-2-aminocyclopropyl]phenyl]benzamide | 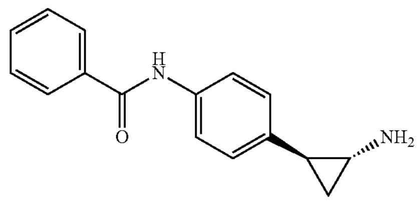 [SMILES: N[C@@H]1C[C@H]1c1ccc(NC(=O)c2ccccc2)cc1] | 1.56 |
| 1 | N-[4-[trans-2-aminocyclopropyl]phenyl]-4-(4-methylpiperazin-1-yl)benzamide dihydrochloride | 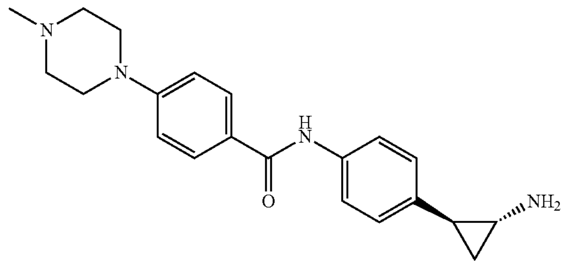 | 3.48 |
| 2 | N-[4-[trans-2-aminocyclopropyl]phenyl]-4-(1-methyl-4-piperidyl)benzamide hydrochloride | 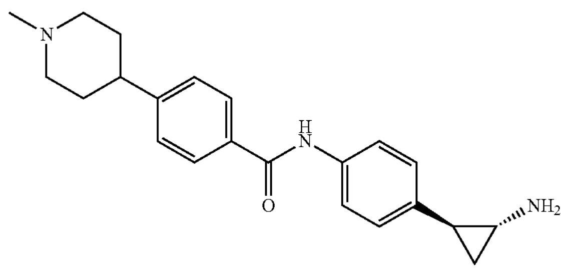 [SMILES: CN1CCC(c2ccc(C(=O)Nc3ccc([C@@H]4C[C@H]4N)cc3)cc2)CC1] | 5.26 |
| 3 | N-[4-[trans-2-aminocyclopropyl]phenyl]-3-(2-oxooxazolidin-3-yl)benzamide hydrochloride | 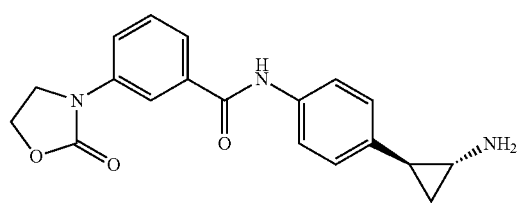 [SMILES: N[C@@H]1C[C@H]1c1ccc(NC(=O)c2cccc(N3CCOC3=O)c2)cc1] | 3.30 |
| 6 | benzyl N-[4-[[4-[trans-2-aminocyclopropyl]phenyl]carbamoyl]-2-(4-methylpiperazin-1-yl)phenyl]carbamate dihydrochloride | 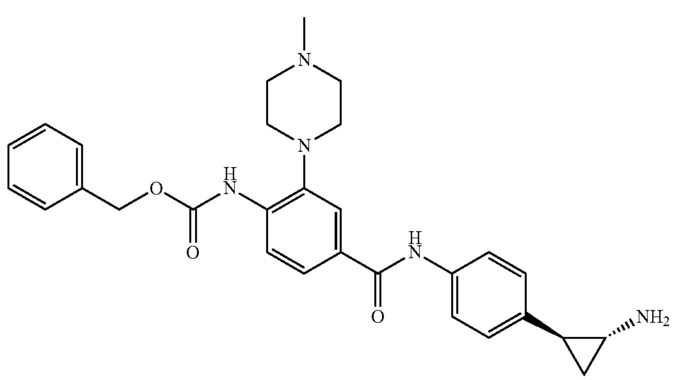 [SMILES: CN1CCN(c2cc(C(=O)Nc3ccc([C@@H]4C[C@H]4N)cc3)ccc2NC(=O)OCc2ccccc2)CC1] | 15.3 |

TABLE 8-continued

| Cpd | Name | Structure | IC$_{50}$ (MAO-A)/ IC$_{50}$ (LSD1) |
|---|---|---|---|
| 7 | benzyl N-[5-[[4-[(trans-2-aminocyclopropyl]phenyl]carbamoyl]-2-(4-methylpiperazin-1-yl)phenyl]carbamate dihydrochloride | 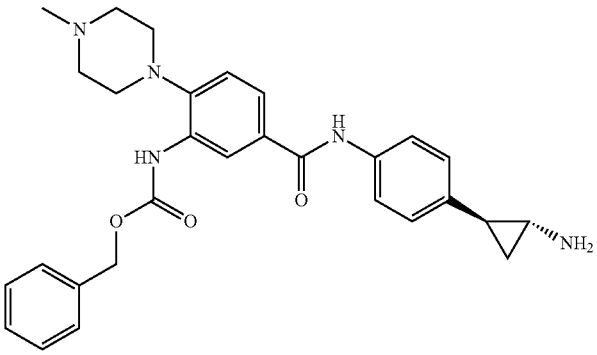 [SMILES: CN1CCN(c2ccc(C(=O)Nc3ccc([C@@H]4C[C@H]4N)cc3)cc2NC(=O)OCc2ccccc2)CC1] | 11.2 |
| 8 | benzyl N-[5-[[4-[trans-2-aminocyclopropyl]phenyl]carbamoyl]-2-(1-piperidyl)phenyl]carbamate hydrochloride | 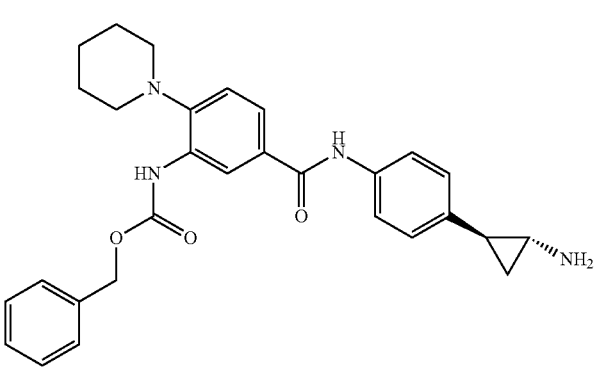 [SMILES: N[C@@H]1C[C@H]1c1ccc(NC(=O)c2ccc(N3CCCCC3)c(NC(=O)OCc3ccccc3)c2)cc1] | 2.23 |
| 9 | benzyl N-[5-[[4-[trans-2-aminocyclopropyl]phenyl]carbamoyl]-2-morpholino-phenyl]carbamate hydrochloride | 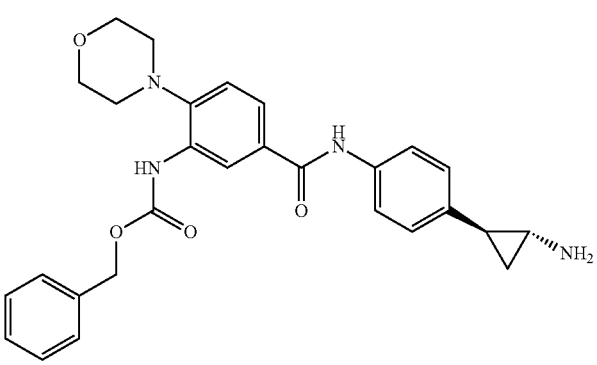 | 3.17 |
| 10 | N-[4-[(1S,2R)-2-aminocyclopropyl]phenyl]-4-(4-methylpiperazin-1-yl)benzamide dihydrochloride | 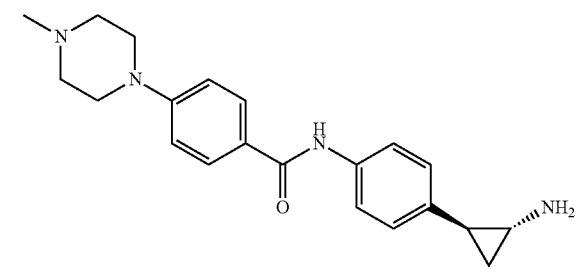 [SMILES: CN1CCN(c2ccc(C(=O)Nc3ccc([C@@H]4C[C@H]4N)cc3)cc2)CC1] | 3.65 |
| 11 | N-[4-[(1S,2R)-2-aminocyclopropyl]phenyl]-3-(2-oxooxazolidin-3-yl)benzamide hydrochloride | 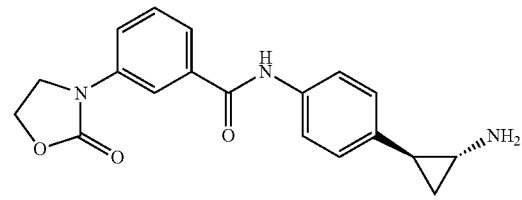 [SMILES: N[C@@H]1C[C@H]1c1ccc(NC(=O)c2cccc(N3CCOC3=O)c2)cc1] | 5.93 |

TABLE 8-continued

| Cpd | Name | Structure | IC$_{50}$ (MAO-A)/ IC$_{50}$ (LSD1) |
|---|---|---|---|
| 13 | N-[4-[(1R,2S)-2-aminocyclopropyl]phenyl]-3-(2-oxooxazolidin-3-yl)benzamide hydrochloride | 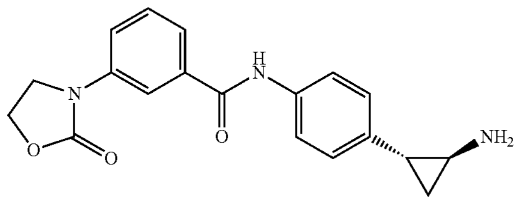 [SMILES: N[C@H]1C[C@@H]1c1ccc(NC(=O)c2cccc(N3CCOC3=O)c2)cc1] | 2.67 |

*compound 5b of WO2011/131576

Compound 5e disclosed in WO2011/131576 was found inactive on KDM1A (LSD1), it displayed MAO-A inhibition with an IC$_{50}$ value of 0.054 μM. Compounds 1-2 and 6-13 have MAO-A inhibition with IC$_{50}$ values greater than 0.1 μM.

Further, the compounds of the disclosure display selectivity over MAO-B with a ratio of IC$_{50}$s MAO-B/LSD1 greater than 100, with the exception of examples 4 and 5 which display a selectivity greater than 10.

2.4 THP-1 Target Modulation

To verify the ability of compounds to be able to inhibit KDM1A in cells, the changes in the mRNA levels of macrophage-specific genes (CD14) were followed considering experimental evidences, which support the ability of KDM1A in regulating macrophage differentiation (Harris, W J et al. Cancer Cell. 2012, 21, 473-487)).

KDM1A has been shown to be involved in the regulation of macrophage differentiation (Harris, W J et al. Cancer Cell. 2012, 21, 473-487). In particular, it has been found that KDM1A inhibitors lead to changes in the mRNA cellular levels of macrophage-specific genes (CD14). CD14—among other genes—is upregulated during monocyte/macrophage differentiation.

For this scope THP-1 cells (ACC 16: DSMZ Leibniz Institute DSMZ German collection of Microorganism and cell culture) were plated at cellular density of 50.000 cells/mL and were incubated with the inhibitor at a fixed concentration of 0.1 μM for 5 days. Then, the cells were recovered and mRNA extracted to follow mRNA levels of the macrophage-specific genes CD14. mRNA expression was measured by quantitative RT-PCR (Fast SYBR Green Master mix, Applied Biosystems Foster City, Calif.) using specific primers and normalized against TBP mRNA. Results are presented as fold induction relative to vehicle treated cells (DMSO). Primers used in this study were:

```
TBP:
                                     (SEQ ID NO: 1)
    GCTGGCCCATAGTGATCTTT- (SEQ ID NO: 2)
    CTTCACACGCCAAGAAACAGT

CD14:
                                     (SEQ ID NO: 3)
    GTTCGGAAGACTTATCGACCA- (SEQ ID NO: 4)
    ATCGTCCAGCTCACAAGGTT
```

TABLE 9

| Cpd | Name | Target modulation CD14 mRNA expression (fold increase versus vehicle) |
|---|---|---|
| 1 | N-[4-[trans-2-aminocyclopropyl]phenyl]-4-(4-methylpiperazin-1-yl)benzamide dihydrochloride | 27.9 |
| 5e* | N-[4-[trans-2-aminocyclopropyl]phenyl]-4-phenyl-benzamide | 2.2 |
| 2 | N-[4-[trans-2-aminocyclopropyl]phenyl]-4-(1-methyl-4-piperidyl)benzamide hydrochloride | 21.8 |
| 3 | N-[4-[trans-2-aminocyclopropyl]phenyl]-3-(2-oxooxazolidin-3-yl)benzamide hydrochloride | 21.2 |
| 6 | benzyl N-[4-[[4-[trans-2-aminocyclopropyl]phenyl]carbamoyl]-2-(4-methylpiperazin-1-yl)phenyl]carbamate dihydrochloride | 13 |
| 10 | N-[4-[(1S,2R)-2-aminocyclopropyl]phenyl]-4-(4-methylpiperazin-1-yl)benzamide dihydrochloride | 20.1 |
| 11 | N-[4-[(1S,2R)-2-aminocyclopropyl]phenyl]-3-(2-oxooxazolidin-3-yl)benzamide hydrochloride | 15.1 |
| 13 | N-[4-[(1R,2S)-2-aminocyclopropyl]phenyl]-3-(2-oxooxazolidin-3-yl)benzamide hydrochloride | 3.1 |

*compound 5e of WO2011/131576

2.5 THP-1 Methylcellulose Assay

The KDM1A inhibitors were tested for their anti-clonogenic potential on human THP-1 cells (ACC 16: DSMZ Leibniz Institute DSMZ German collection of Microorganism and cell culture).

THP-1 cells were plated at a density of 250 cells per plate and cultured with the inhibitors at a fixed dose of 500 nM in MethoCult™ H4435 Enriched medium (StemCell Technologies, Vancouver, BC) for 13 days according to the manufacturer instructions. Then, the colony forming potential was scored by direct visualization using an inverted microscope and the percentage of inhibition over the vehicle was assessed. In addition, the cells were harvested and compounds-induced maturation was monitored by changes in the mRNA levels of macrophage-specific genes (CD14) as reported above.

TABLE 10

| Cpd | Name | Colony formation % of Inhibition | Colony formation Target Modulation CD14 mRNA expression (Fold increase) |
|---|---|---|---|
| 1 | N-[4-[trans-2-aminocyclopropyl]phenyl]-4-(4-methylpiperazin-1-yl)benzamide dihydrochloride | 65 | 67 |
| 3 | N-[4-[trans-2-aminocyclopropyl]phenyl]-3-(2-oxooxazolidin-3-yl)benzamide hydrochloride | 41 | 24.8 |
| 10 | N-[4-[(1S,2R)-2-aminocyclopropyl]phenyl]-4-(4-methylpiperazin-1-yl)benzamide dihydrochloride | 60 | 67 |
| 11 | N-[4-[(1S,2R)-2-aminocyclopropyl]phenyl]-3-(2-oxooxazolidin-3-yl)benzamide hydrochloride | 36.3 | 27.7 |
| 12 | N-[4-[(1R,2S)-2-aminocyclopropyl]phenyl]-4-(4-methylpiperazin-1-yl)benzamide dihydrochloride | 15 | 4 |
| 13 | N-[4-[(1R,2S)-2-aminocyclopropyl]phenyl]-3-(2-oxooxazolidin-3-yl)benzamide hydrochloride | 19 | 6 |

2.6 In Vivo Activity

The in vivo activity was conducted on a mouse model as characterized by Minucci et al. (Minucci S. et al. Blood 2002, 100, 2989-2995). The model is characterized by the development of leukemia, resembling the human acute promyelocytic leukemia, which is associated to a blast infiltration of several organs as bone marrow, liver and particularly of the spleen.

Figure 1B:
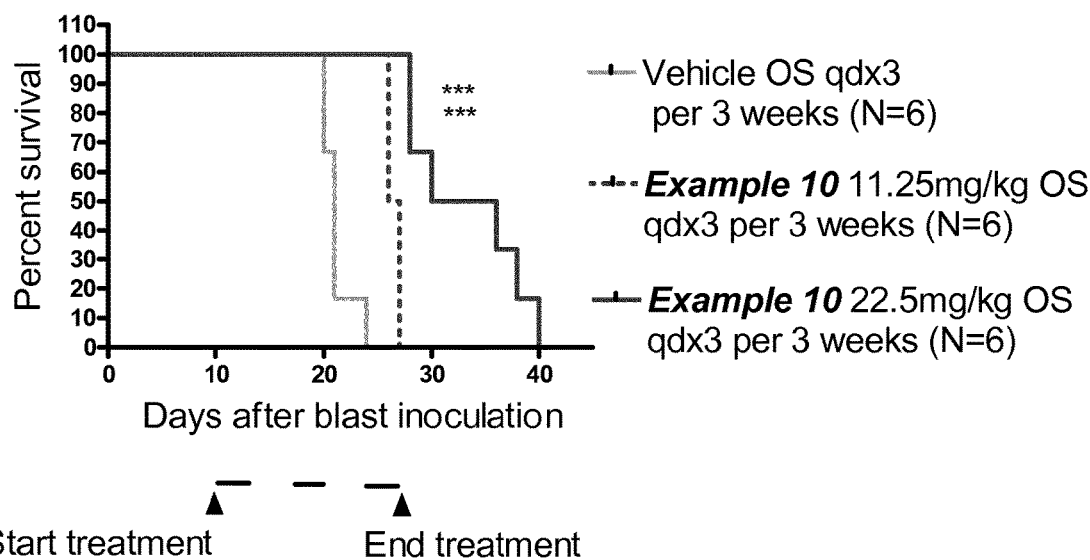

For the in vivo analysis, one million of leukemic cells (obtained from 129SvEv mice, Minucci S. et al. Blood 2002, 100, 2989-2995, obtained from Taconic, One Hudson City Centre Hudson, N.Y. (USA)) were injected intravenously into non-irradiated syngenic recipients. Mice were randomized in experimental groups of at least 6 mice and the treatment started once blast cells are detected in the recipients' peripheral blood (10 days after injection). N-[4-[trans-2-aminocyclopropyl]phenyl]-4-(4-methylpiperazin-1-yl) benzamide dihydrochloride (Example 1) was dissolved in a vehicle comprising 40% PEG 400 in 5% glucose solution and orally administered for 5 days per week for 2 weeks at the doses of 27 mg/kg and for 3 days per week for 2 weeks at the dose of 45 mg/kg. The survival of mice of the different experimental groups, represented by a Kaplan-Meier survival plot, was analyzed and reported in the graph. A significant increase of survival was obtained at the two tested doses (FIG. 1A). N-[4-[(1S,2R)-2-aminocyclopropyl] phenyl]-4-(4-methylpiperazin-1-yl)benzamide dihydrochloride (Example 10) was dissolved in a vehicle comprising 40% PEG 400 in a 5% glucose solution and orally administered for 3 days per week for 3 weeks at the doses of 11.25 mg/kg and 22.5 mg/kg. The survival of mice of the different experimental groups, represented by a Kaplan-Meier survival plot, was analyzed and reported in the graph. A significant dose dependent increase of survival was obtained (FIG. 1B).

2.7 In Vivo Target Modulation Assay

Figure 2A:
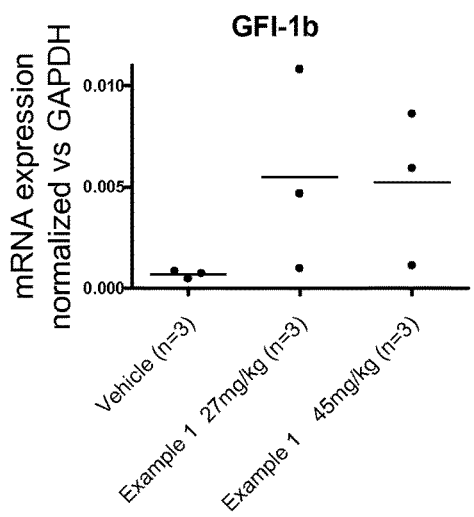
FIG. 2: A) Quantitative real-time PCR analysis of GFI-1B mRNA expression in leukemic cells recovered from infiltrated spleen at three days after starting in vivo treatment with compound 1, N-[4-[trans-2-aminocyclopropyl]phenyl]-4-(4-methylpiperazin-1-yl)benzamide dihydrochloride. Increased mRNA expression of GFI-1B in cells recovered from spleen of leukemic mice is observed in the treated group. B) Quantitative real-time PCR analysis of GFI-1B mRNA expression in leukemic cells recovered from infiltrated spleen at three days after starting in vivo treatment with compound 10, N-[4-[(1S,2R)-2-aminocyclopropyl]phenyl]-4-(4-methylpiperazin-1-yl)benzamide dihydrochloride. Increased mRNA expression of GFI-1B in cells recovered from spleen of leukemic mice is observed in the treated group.
Figure 2B:
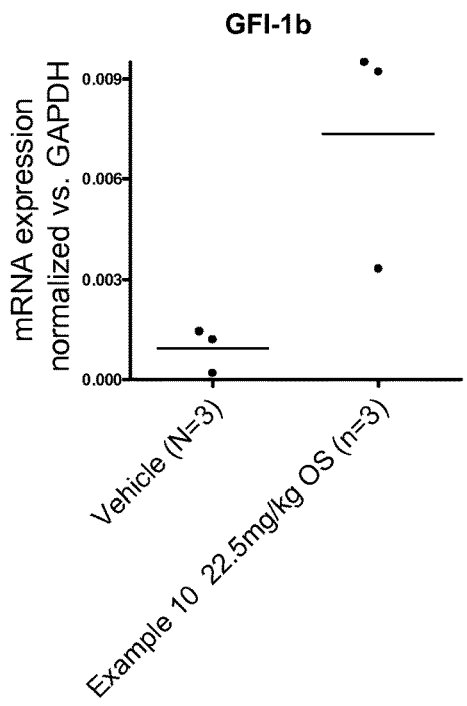

Transcription induction of Gfi-1b was followed in cells recovered from spleen of leukemic mice sacrificed after 3 days of treatment in order to verify the ability to inhibit KDM1A. The choice to follow the effect on Gfi-1 b, a gene associated with haematopoietic differentiation, was based on the observation that GFI-1b levels are increased following KDM1A deletion and that the gene is a direct transcriptional target of KDM1A (Saleque, S. et al. Mol. Cell, 27 (2007), pp. 562-572). 3 mice per experimental group were sacrificed after 3 days of treatment with example 1, administered orally at the doses of 27 and 45 mg/kg, with example 10, administered orally at the dose of 22.5 mg/kg. Cells were obtained from the spleen and the total RNA was purified using RNeasy Mini Kit (Qiagen, Valencia, Calif.), quantified and reverse transcribed. mRNA levels were measured by quantitative RT-PCR (Fast SYBR Green Master mix, Applied Biosystems Foster City, Calif.) using specific primers and normalized against GADPH mRNA. Results are presented as fold induction relative to vehicle (FIGS. 2A and 2B) Primers used in this study were:

```
GFI1b:
                                       (SEQ ID NO: 5)
GAGATGTTGCTGAACCAGAGC- (SEQ ID NO: 6)
TTGGGGTGTCACGAGAGG

GADPH:
                                       (SEQ ID NO: 7)
AACTTTGGCATTGTGGAAGG- (SEQ ID NO: 8)
CACATTGGGGGTAGGAACAC
```

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims. It will be understood by those skilled in the art that various changes in form and details may be made therein without departing from the scope of the invention encompassed by the appended claims.

The invention claimed is:

1. A compound of formula (I)

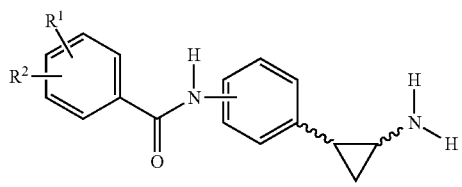

or a pharmaceutically acceptable salt, solvate, or prodrug thereof, wherein:

$R^1$ is pyrrolidinyl, 1-methylpiperidin-4-yl, piperazinyl, tetrahydrofuranyl, tetrahydropyranyl, morpholinyl, thiomorpholinyl, tetrahydroquinolinyl, tetrahydroisoquinolinyl, tetrahydroquinoxalinyl, benzodioxolyl, 2,3-dihydro-benzodioxinyl, benzoxazolyl, azepinyl, diazapinyl or 2-oxazolidinyl, wherein $R^1$ is unsubstituted or substituted by one or more $C_1$-$C_6$ alkyl or oxo;

$R^2$ is hydrogen, halogen, $C_1$-$C_6$ alkyl, $C_1$-$C_6$ alkoxy, $C_1$-$C_6$ haloalkyl, $C_1$-$C_6$ haloalkoxy, or benzyloxycarbonylamino.

2. The compound according to claim 1, wherein $R^1$ is 4-methylpiperazin-1-yl or 2-oxazolidin-3-yl.

3. The compound according to claim 1, wherein $R^2$ is selected from the group consisting of hydrogen and benzyloxycarbonylamino.

4. The compound according to claim 1, wherein $R^2$ is hydrogen.

5. The compound according to claim 1, wherein $R^2$ is benzyloxycarbonylamino.

6. The compound of claim 1, wherein $R^1$ is 4-methylpiperazin-1-yl and $R^2$ is hydrogen.

7. The compound of claim 1, wherein $R^1$ is 4-methylpiperazin-1-yl and $R^2$ is benzyloxycarbonylamino.

8. The compound of claim 1, wherein $R^1$ is 1-methylpiperidin-4-yl and $R^2$ is hydrogen.

9. The compound of claim 1, wherein $R^1$ is 1-methylpiperidin-4-yl and $R^2$ is benzyloxycarbonylamino.

10. The compound of claim 1, wherein $R^1$ is 2-oxazolidin-3-yl and $R^2$ is hydrogen.

11. The compound of claim 1, wherein $R^1$ is 2-oxazolidin-3-yl and $R^2$ is benzyloxycarbonylamino.

12. A compound selected from:
N-[4-[trans-2-aminocyclopropyl]phenyl]-4-(4-methylpiperazin-1-yl)benzamide;
N-[4-[trans-2-aminocyclopropyl]phenyl]-4-(1-methyl-4-piperidyl)benzamide;
N-[4-[trans-2-aminocyclopropyl]phenyl]-3-(2-oxazolidin-3-yl)benzamide;
N-[4-[trans-2-aminocyclopropyl]phenyl]-4-morpholinobenzamide;
N-[4-[trans-2-aminocyclopropyl]phenyl]-4-(2-oxazolidin-3-yl)benzamide;
benzyl N-[5-[[4-[(trans-2-aminocyclopropyl]phenyl]carbamoyl]-2-(4-methylpiperazin-1-yl)phenyl]carbamate;
benzyl N-[4-[[4-[trans-2-aminocyclopropyl]phenyl]carbamoyl]-2-(4-methylpiperazin-1-yl)phenyl]carbamate;
benzyl N-[5-[[4-[trans-2-aminocyclopropyl]phenyl]carbamoyl]-2-(1-piperidyl)phenyl]carbamate;
benzyl N-[5-[[4-[trans-2-aminocyclopropyl]phenyl]carbamoyl]-2-morpholino-phenyl]carbamate;
N-[4-[(1S,2R)-2-aminocyclopropyl]phenyl]-4-(4-methylpiperazin-1-yl)benzamide;
N-[4-[(1S,2R)-2-aminocyclopropyl]phenyl]-3-(2-oxazolidin-3-yl)benzamide;
N-[4-[(1R,2S)-2-aminocyclopropyl]phenyl]-4-(4-methylpiperazin-1-yl)benzamide;
N-[4-[(1R,2S)-2-aminocyclopropyl]phenyl]-3-(2-oxazolidin-3-yl)benzamide; and a pharmaceutically acceptable salt, solvate, or prodrug thereof.

13. A pharmaceutical composition comprising a compound according to claim 1 together with a pharmaceutically acceptable excipient and/or diluent.

14. The pharmaceutical composition according to claim 13 further comprising at least one therapeutic agent selected from the group consisting of histone deacetylase inhibitors, retinoid receptor modulators, antiproliferative/antineoplastic agents, cytostatic agents, agents which inhibit cancer cell invasion, inhibitors of growth factor function, antiangiogenic agents, cell cycle inhibitors, proteasome inhibitors, HSP90 inhibitors, selective COX-2 inhibitors, and a chemotherapeutic agent.

15. The pharmaceutical composition according to claim 13 in the form of tablets, capsules, oral preparations, powders, granules, pills, injectable or infusible liquid, solutions, suspensions, emulsions, suppositories, ointments, creams, lotions, gels, pastes, or transdermal delivery devices.

16. A method of treating acute myeloid leukemia, chronic myeloid leukemia, acute lymphoblastic leukemia, chronic lymphoblastic leukemia, myelodysplastic syndrome, multiple myeloma, Hodgkin's disease, non-Hodgkin's lymphoma, cutaneous T-cell lymphoma, peripheral T-cell lymphoma, adult T-cell leukemia, large B-cell lymphoma, a mammary tumor, a pulmonary tumor, a skin tumor, osteosarcoma, fibrosarcoma, rhabdomyosarcoma, neuroblastoma, glioblastoma, a cerebral tumor, head and neck cancer, colon cancer, a gastric tumor, gastrointestinal adenocarcinoma, hepatocellular carcinoma, pancreatic carcinoma, a renal tumor, teratocarcinoma, embryonic carcinoma, HIV, herpes virus infection, or obesity in a subject comprising administering to the subject an effective amount of a compound of claim 1 or pharmaceutical composition thereof.

17. A method of treating pleural mesothelioma, adenocarcinoma, non-small lung cancer, small-cell lung cancer, basal cell carcinoma, melanoma, squamous cell carcinoma, Kaposi's sarcoma, keratocanthoma, a testicular tumor, an ovarian tumor, cervical carcinoma, an endometrial tumor, a prostate tumor, or thyroid carcinoma in a subject comprising administering to the subject an effective amount of a compound of claim 1 or pharmaceutical composition thereof.

18. A method of treating leukemia, non-small cell lung cancer, hepatocellular carcinoma, or glioblastoma in a subject comprising administering to the subject in need of such treating or presenting an effective amount of a compound of claim 1 or pharmaceutical composition thereof.

19. The method of claim 18, wherein the glioblastoma is giant cell glioblastoma or gliosarcoma.

20. The method of claim 18, wherein the leukemia is acute myeloid leukemia.

21. A method of treating a KDM1-mediated disease or disorder whereby treatment is achieved by inhibiting KDM1 in a subject, comprising administering to the subject in need of such treatment an effective amount of a compound of claim 1, or a pharmaceutical composition thereof, that inhibits the activity or expression of KDM1.

22. A process for obtaining a compound of formula (I) according to claim 1, the process comprising the preparation of a compound of formula A2 by reaction of a compound of formula A1 with a suitable azide and in the presence of a base; the reaction of a compound of formula A2 with an amide A3 and CuI (copper(I) iodide) in presence of a base to obtain a compound of formula A4; and the deprotection of a compound of formula A4 to obtain a compound of formula (I), as represented below:

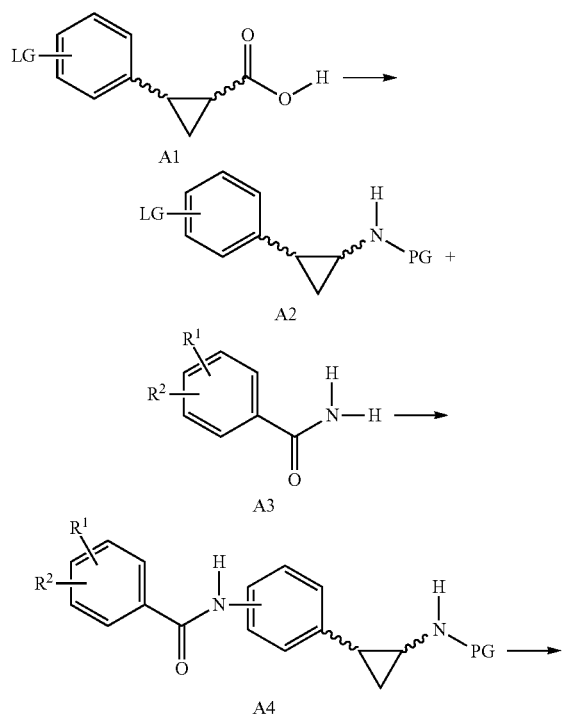

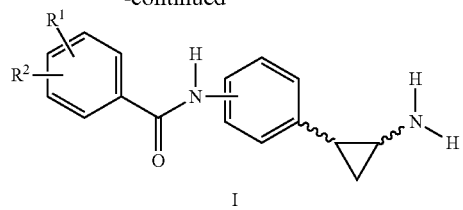

wherein $R^1$ and $R^2$ are as defined in claim 1, PG is a protecting group, and LG is a leaving group.

23. The process according to claim 22, wherein PG is carboxybenzyl, tert-butyloxycarbonyl (BOC), or 9-fluorenylmethyloxycarbonyl.

24. The process according to claim 22, wherein LG is bromide, iodide, or chloride.

25. A process for obtaining a compound of formula (I) according to claim 1, the process comprising the preparation of compounds of formula B3 by reaction of a compound of formula B1 with compound of formula B2 and in presence of a peptide coupling reagent, and the deprotection of a compound of formula B3 to obtain a compound of formula (I), as represented below:

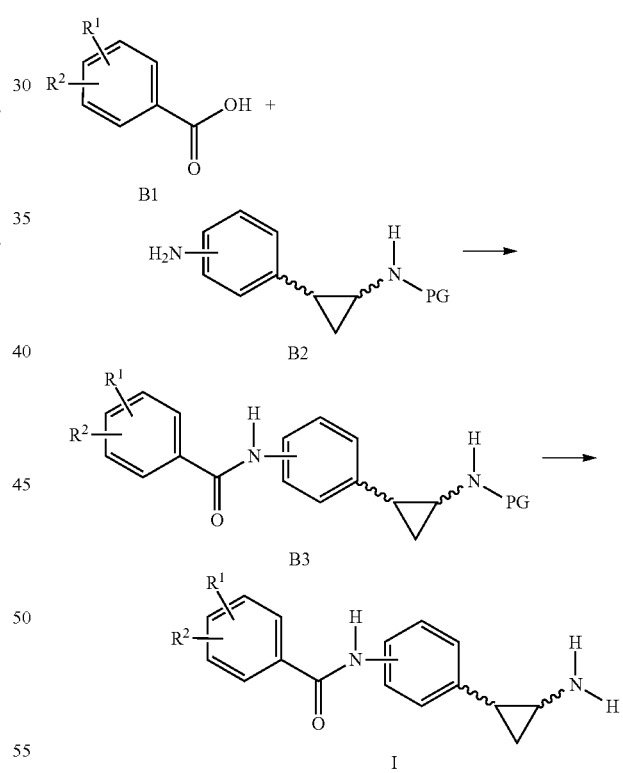

wherein $R^1$ and $R^2$ are as defined in claim 1, PG is carboxybenzyl, tert-butyloxycarbonyl (BOC), or 9-fluorenylmethyloxycarbonyl.

26. A compound selected from N-[4-[trans-2-aminocyclopropyl]phenyl]-4-(4-methylpiperazin-1-yl)benzamide, N-[4-[(1S,2R)-2-aminocyclopropyl]phenyl]-4-(4-methylpiperazin-1-yl)benzamide, and a pharmaceutically acceptable salt, solvate, or prodrug thereof.

27. The compound of claim 26, wherein the compound is a dihydrochloride salt.

28. A method of treating acute myeloid leukemia, chronic myeloid leukemia, acute lymphoblastic leukemia, chronic lymphoblastic leukemia, myelodysplastic syndrome, multiple myeloma, Hodgkin's disease, non-Hodgkin's lymphoma, cutaneous T-cell lymphoma, peripheral T-cell lymphoma, adult T-cell leukemia, large B-cell lymphoma, a mammary tumor, a pulmonary tumor, a skin tumor, osteosarcoma, fibrosarcoma, rhabdomyosarcoma, neuroblastoma, glioblastoma, a cerebral tumor, head and neck cancer, colon cancer, a gastric tumor, gastrointestinal adenocarcinoma, hepatocellular carcinoma, pancreatic carcinoma, a renal tumor, teratocarcinoma, embryonic carcinoma, HIV, herpes virus infection, or obesity in a subject comprising administering to the subject an effective amount of a compound of claim 26 or pharmaceutical composition thereof.

29. A method of treating leukemia, non-small cell lung cancer, hepatocellular carcinoma, or glioblastoma in a subject comprising administering to the subject in need of such treating or presenting an effective amount of a compound of claim 26 or pharmaceutical composition thereof.

30. The method of claim 29, wherein the glioblastomas is giant cell glioblastoma or gliosarcoma.

31. The method of claim 29, wherein the leukemia is acute myeloid leukemia.

32. A method of treating pleural mesothelioma, adenocarcinoma, non-small lung cancer, small-cell lung cancer, basal cell carcinoma, melanoma, squamous cell carcinoma, Kaposi's sarcoma, keratocanthoma, a testicular tumor, an ovarian tumor, cervical carcinoma, an endometrial tumor, a prostate tumor, or thyroid carcinoma in a subject comprising administering to the subject an effective amount of a compound of claim 26 or pharmaceutical composition thereof.

\* \* \* \* \*

SEQUENCE LISTING

<160> NUMBER OF SEQ ID NOS: 8

<210> SEQ ID NO 1
<211> LENGTH: 20

```
<212> TYPE: DNA
<213> ORGANISM: Artificial Sequence
<220> FEATURE:
<223> OTHER INFORMATION: synthetic primer

<400> SEQUENCE: 1
gctggcccat agtgatcttt                                                   20

<210> SEQ ID NO 2
<211> LENGTH: 21
<212> TYPE: DNA
<213> ORGANISM: Artificial Sequence
<220> FEATURE:
<223> OTHER INFORMATION: synthetic primer

<400> SEQUENCE: 2
cttcacacgc caagaaacag t                                                 21

<210> SEQ ID NO 3
<211> LENGTH: 21
<212> TYPE: DNA
<213> ORGANISM: Artificial Sequence
<220> FEATURE:
<223> OTHER INFORMATION: synthetic primer

<400> SEQUENCE: 3
gttcggaaga cttatcgacc a                                                 21

<210> SEQ ID NO 4
<211> LENGTH: 20
<212> TYPE: DNA
<213> ORGANISM: Artificial Sequence
<220> FEATURE:
<223> OTHER INFORMATION: synthetic primer

<400> SEQUENCE: 4
atcgtccagc tcacaaggtt                                                   20

<210> SEQ ID NO 5
<211> LENGTH: 21
<212> TYPE: DNA
<213> ORGANISM: Artificial Sequence
<220> FEATURE:
<223> OTHER INFORMATION: synthetic primer

<400> SEQUENCE: 5
gagatgttgc tgaaccagag c                                                 21

<210> SEQ ID NO 6
<211> LENGTH: 18
<212> TYPE: DNA
<213> ORGANISM: Artificial Sequence
<220> FEATURE:
<223> OTHER INFORMATION: synthetic primer

<400> SEQUENCE: 6
ttggggtgtc acgagagg                                                     18

<210> SEQ ID NO 7
<211> LENGTH: 20
<212> TYPE: DNA
<213> ORGANISM: Artificial Sequence
<220> FEATURE:
<223> OTHER INFORMATION: synthetic primer

<400> SEQUENCE: 7
```

```
aactttggca ttgtggaagg                                      20

<210> SEQ ID NO 8
<211> LENGTH: 20
<212> TYPE: DNA
<213> ORGANISM: Artificial Sequence
<220> FEATURE:
<223> OTHER INFORMATION: synthetic primer

<400> SEQUENCE: 8
cacattgggg gtaggaacac                                      20
```